(12) United States Patent
Yuan et al.

(10) Patent No.: US 7,534,565 B2
(45) Date of Patent: *May 19, 2009

(54) DLC-1 GENE DELETED IN CANCERS

(75) Inventors: Bao-Zhu Yuan, Columbia, MD (US); Snorri S. Thorgeirsson, Bethesda, MD (US); Nicholas Popescu, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 220 days.

This patent is subject to a terminal disclaimer.

(21) Appl. No.: 10/995,914

(22) Filed: Nov. 22, 2004

(65) Prior Publication Data

US 2005/0106616 A1 May 19, 2005
US 2005/0227255 A9 Oct. 13, 2005

Related U.S. Application Data

(63) Continuation of application No. 09/644,947, filed on Aug. 23, 2000, now Pat. No. 6,897,018.

(60) Provisional application No. 60/075,952, filed on Feb. 25, 1998.

(51) Int. Cl.
*C12Q 1/68* (2006.01)

(52) U.S. Cl. ............... 435/6; 435/91.2; 436/64; 536/23.1

(58) Field of Classification Search ............ 435/6, 435/91.2, 64; 536/23.1
See application file for complete search history.

(56) References Cited

U.S. PATENT DOCUMENTS

| | | | |
|---|---|---|---|
| 5,330,892 A | 7/1994 | Vogelstein et al. | |
| 5,571,905 A | 11/1996 | Vogelstein et al. | |
| 5,576,422 A | 11/1996 | Vogelstein et al. | |
| 5,624,819 A | 4/1997 | Skolnick et al. | |
| 5,654,155 A | 8/1997 | Murphy et al. | |
| 5,693,473 A | 12/1997 | Shattuck-Eidens et al. | |
| 5,693,536 A | 12/1997 | Vogelstein et al. | |
| 5,709,999 A | 1/1998 | Shattuck-Eidens et al. | |
| 5,710,001 A | 1/1998 | Skolnick et al. | |
| 5,912,143 A | 6/1999 | Bandman et al. | |

OTHER PUBLICATIONS

Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Tian, J et al, 2004, Physiol Genomics, 17: 170-182.*
Van Dyke D L et al, 2003, Cancer Genetics and Cytogenetics 241: 137-141.*
Zaslav A L et al, 2002, Amer J Medical Genetics 107: 174-176.*
Kunkel, P, et al, 2001, Neuro-oncology 3(2): 82-88.*
Lewis B, 1983, ed, Genes, John Wiley & Sons, New York, p. 43.*
Guan et al, 2006, Clin Cancer Res, 12(5): 1412-1419.*
Greenbaum et al. (Genome Biology, 2003, vol. 4, Issue 9, pp. 117.1-117.8).*
Fu et al 1996 (EMBO Journal, vol. 15, pp. 4392-4401).*
Yokota, J et al, 1988 (Oncogene, vol. 3, pp. 471-475).*
Alberts et al., *Mol. Biol. Cell*, 3rd edition, 1994, p. 465.
Bergerheim et al., "Deletion mapping of chromosomes 8, 10, and 16 in human prostatic carcinoma," *Genes, Chromosomes & Cancer* 3:215-220 (1991).
Brothman, "Cytogenetic studies in prostate cancer: are we making progress?," *Cancer Genet. Cytogenet.* 95:116-121 (1997).
Cher et al., "Comparative genomic hybridization, allelic imbalance, and fluorescence in situ hybridization on chromosome 8 in prostate cancer," *Genes, Chromosomes & Cancer* 11:153-162 (1994).
Chinen et al., "Isolation of 45 exon-like fragments from 8p22→p21.3, a region that is commonly deleted in hepatocellular, colorectal, and non-small cell lung carcinomas," *Cytogenet. Cell Genet.* 75:190-196 (1996).
Drexler et al., "Recent results on the biology of Hodgkin and Reed-Sternberg cells," *Leuk. Lymphoma* 9:1-25 (1993).
Embleton et al., "Monoclonal antibodies to osteogenic sarcoma antigens," *Immunol. Ser.* 23:181-207 (1984).
Emi et al., "Allelic loss at chromosome band 8p21.3-p22 is associated with progression of hepatocellular carcinoma," *Genes Chromosom. Cancer* 7:152-157 (1993).
Friend et al., "Emerging uses for genomic information in drug discovery," *N. Engl. J. Med.* 338:125-126 (1998).
Fu et al., "Translational regulation of human p53 gene expression," *EMBO J.* 15:4392-4401 (1996).
Guo et al., "Induction profile of rat organic anion transporting polypeptide 2 (oatp2) by prototypical drug-metabolizing enzyme inducers that activate gene expression through ligand-activated transcription factor pathways," *J. Pharmacol. Exp. Ther.* 300:206-212 (2002).
Hell et al., "Hodgkin cells accumulate mRNA for *bcl-2*," *Lab. Invest.* 73:492-496 (1995).

(Continued)

Primary Examiner—Larry R. Helms
Assistant Examiner—Minh-Tam Davis
(74) Attorney, Agent, or Firm—Klarquist Sparkman, LLP.

(57) ABSTRACT

A cDNA molecule corresponding to a newly discovered human gene is disclosed. The new gene, which is frequently deleted in liver cancer cells and cell lines, is called the DLC-1 gene. Because the gene is frequently deleted in liver cancer cells, but present in normal cells, it is thought to act as a tumor suppressor. This gene is also frequently deleted in breast and colon cancers, and its expression is decreased or undetectable in many prostate and colon cancers. Also disclosed is the amino acid sequence of the protein encoded by the DLC-1 gene. Methods of using these biological materials in the diagnosis and treatment of hepatocellular cancer, breast cancer, colon cancer, prostate cancer, and adenocarcinomas are presented.

16 Claims, 6 Drawing Sheets

OTHER PUBLICATIONS

Homma et al., "A dual functional signal mediator showing RhoGAP and Phospholipase C-δ stimulating activities," *EMBO J.* 14:286-291 (1995).

Hsu, in *Tissue Culture Methods and Applications*, Kruse and Patterson (eds.), p. 764, Academic Press, NY (1973).

Isola et al., "Genetic aberrations detected by comparative genomic hybridization predict outcome in node-negative breast cancer," *Am. J. Pathol.* 147:905-911 (1995).

Jansen et al., "Translational control of gene expression," *Pediatric Res.* 37:681-686 (1995).

Lewin, ed., *Genes*, p. 42, John Wiley & Sons, New York (1983).

Marchio et al., "Recurrent chromosomal abnormalities in hepatocellular carcinoma detected by comparative genomic hybridization," *Genes Chromosom. Cancer* 18:59-65 (1997).

McClean and Hill, "Evidence of post-translational regulation of P-glycoprotein associated with the expression of a distinctive multiple drug-resistant phenotype in Chinese hamster ovary cells," *Eur. J. Cancer* 29A:2243-2248 (1993).

Ng et al., "*DLC-1* is Deleted in Primary Hepatocellular Carcinoma and Exerts Inhibitory Effects on the Proliferation of Hepatoma Cell Lines with Deleted *DLC-1*-[1]," *Can. Res.* 60:6581-6584 (2000).

Park et al., "DNA variants of DLC-1, a candidate tumor suppressor gene in human hepatocellular carcinoma," *Int. J. Oncol.* 23:133-137 (2003).

Plaumann et al., "Analysis of DLC-1 expression in human breast cancer," *J. Cancer Res. Clin. Oncol.* 129:349-354 (2003).

Shantz and Pegg, "Translational regulation of ornithine decarboxylase and other enzymes of the polyamine pathway," *Int. J. Biochem. Cell Biol.* 31:107-122 (1999).

Symons, "Rho Family GTPases: the cytoskeleton and beyond," *TIBS* 21:178-181 (1996).

Visakorpi et al., "Genetic changes in primary and recurrent prostate cancer by comparative genomic hybridization," *Cancer Res.* 55:342-347 (1995).

Wei et al., "Cloning and Molecular Characterization of the Human Ortholog of the Rat Dual Regulator p122RhoGAP," *EMBL Database Entry AF026219* (Abstract, 1977).

Yokota et al., "Altered expression of the retinoblastoma (RB) gene in small-cell carcinoma of the lung," *Oncogene* 3:471-475 (1988).

Yuan et al., "*Homo sapiens* deleted in liver cancer-1 (DLC-1) mRNA, complete cds.," *EMBL Database Entry AF035119* (Abstract, 1997).

Yuan et al., "Cloning, Characterization, and Chromosomal Localization of a Gene Frequently Deleted in Human Liver Cancer (DLC-1) Homologous to Rat *RhoGAP*," *Cancer Res.* 58:2196-2199 (1998).

Yuan et al., "Assignment and cloning of mouse Arhgap7 to chromosome 8A4-B2, a conserved syntenic region of human chromosome 8p22-p21," *Cytogenet. Cell Genet.* 87:189-190 (1999).

Yuan et al., "Promoter hypermethylation of DLC-1, a candidate tumor suppressor gene, in several common human cancers," *Cancer Genet. Cytogenet.* 140:113-117 (2003).

Yuan et al., "DLC-1 inhibits human breast cancer cell growth and in vivo tumorigenicity," *Oncogene* 22:445-450 (2003).

Yuan et al., "DLC-1 operates as a tumor suppressor gene in human non-small cell lung carcinomas," *Oncogene* 23:1405-1411 (2004).

Zimmer, "Examination of the calcium-modulated protein S100 alpha and its target proteins in adult and developing skeletal muscle," *Cell Motil. Cytoskeleton* 20:325-337 (1991).

Durkin et al. "DLC-1: a Rho GTPase-activating protein and tumor suppressor," *J. Cell. Mol. Med.*, 11:1185-1207, 2007.

Guan et al. "Aberrant methylation and deacetylation of deleted in liver cancer-1 gene in prostate cancer: Potential clinical applications," *Clin. Cancer Res.*, 12:1412-1419, 2006.

Guan et al., "Adenovirus mediated restoration of expression of the tumor suppressor gene DLC1 inhibits the proliferation and tumorigenicity of aggressive, androgen-independent human prostate cancer cell lines: prospects for gene therapy," *Cancer Gene Therapy*, 15:371:381, 2008.

Park et al. "DNA variants of DLC-1, a candidate tumor suppressor gene in human hepatocellular carcinoma," *Int. J. Oncology*, 23:133-137, 2003.

Qian et al. "Oncogenic inhibition by a deleted in liver cancer gene requires cooperation between tensin binding and Rho-specific GTPase-activating protein activities," *Proc. Natl. Acad. Sci. USA*, 104:9012-9017, 2007.

Ullmannova et al. "Inhibition of cell proliferation, induction of apoptosis, reactivation of DLC1, and modulation of other gene expression by dietary flavone in breast cancer cell lines," *Cancer Detection and Prevention*, 31:110-118, 2007.

Ullmanova et al. "Expression profile of the tumor suppressor genes DLC-1 and DLC-2 in solid tumors," *Int. J. Oncol.*, 29:1127-1132, 2006.

Yuan et al., "DLC-1 gene inhibits human breast cancer cell growth and in vivo tumorigenicity," *Oncogene*, 22:445-450, 2003.

Yuan et al., "DLC-1 operates as a tumor suppressor gene in human non-small cell lung carcinomas," *Oncogene*, 23:1405-1411, 2004.

Yuan et al., "Morphological changes and nuclear translocation of DLC1 tumor suppressor protein precede apoptosis in human non-small cell lung carcinoma cells," *Exp. Cell Res*, 313: 3868-3880, 2007.

Yuan et al., "Promoter hypermethylation of DLC-1, a candidate tumor suppressor gene, in several common human cancers," *Cancer Genet. Cytogenet.*, 140:113-117, 2003.

Zhou et al., "DLC1 suppresses distant dissemination of human hepatocellular carcinoma cells in nude mice through reduction of RhoA GTPase activity, actin cytoskeletal disruption and down regulation of genes involved in metastasis," *Int J. Oncol*, 32(6):1285-1291, 2008.

* cited by examiner

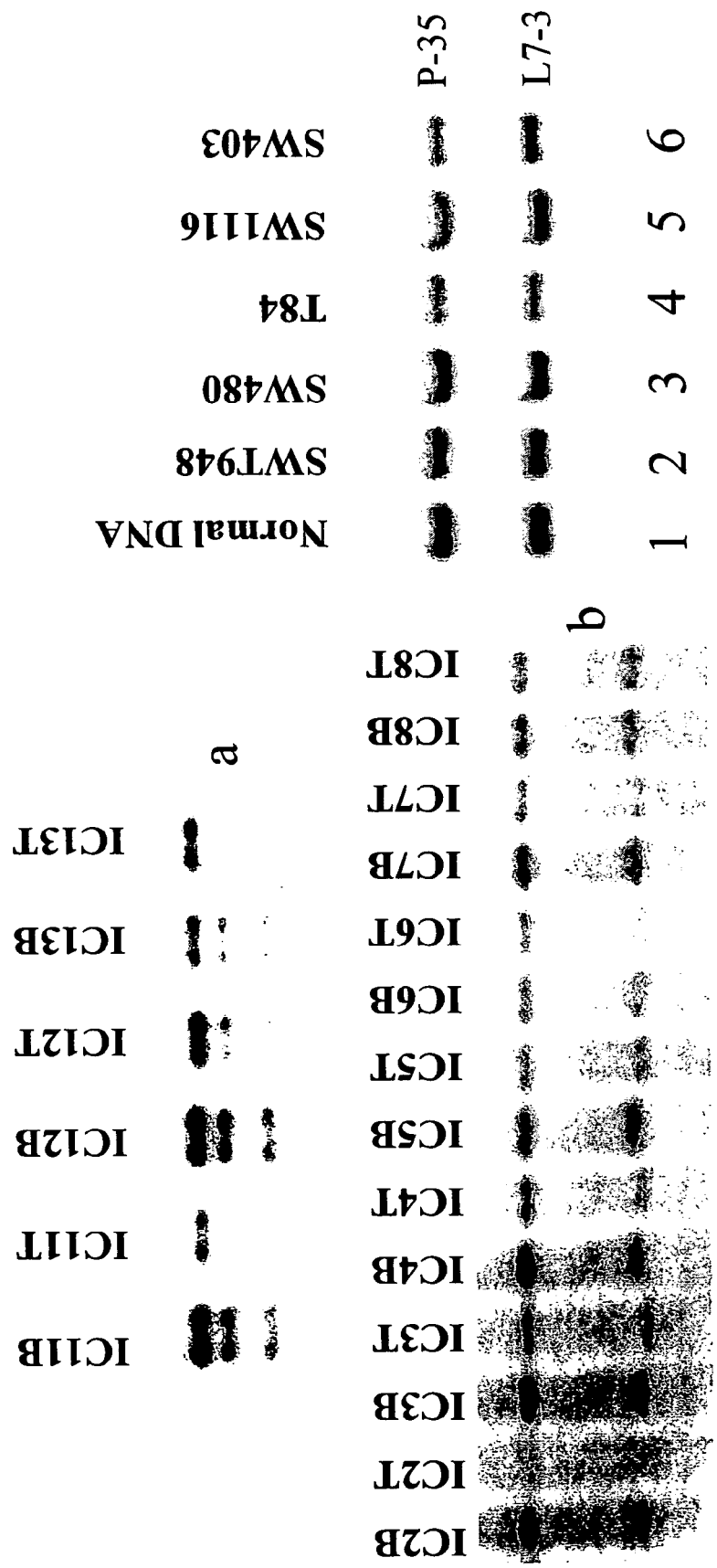

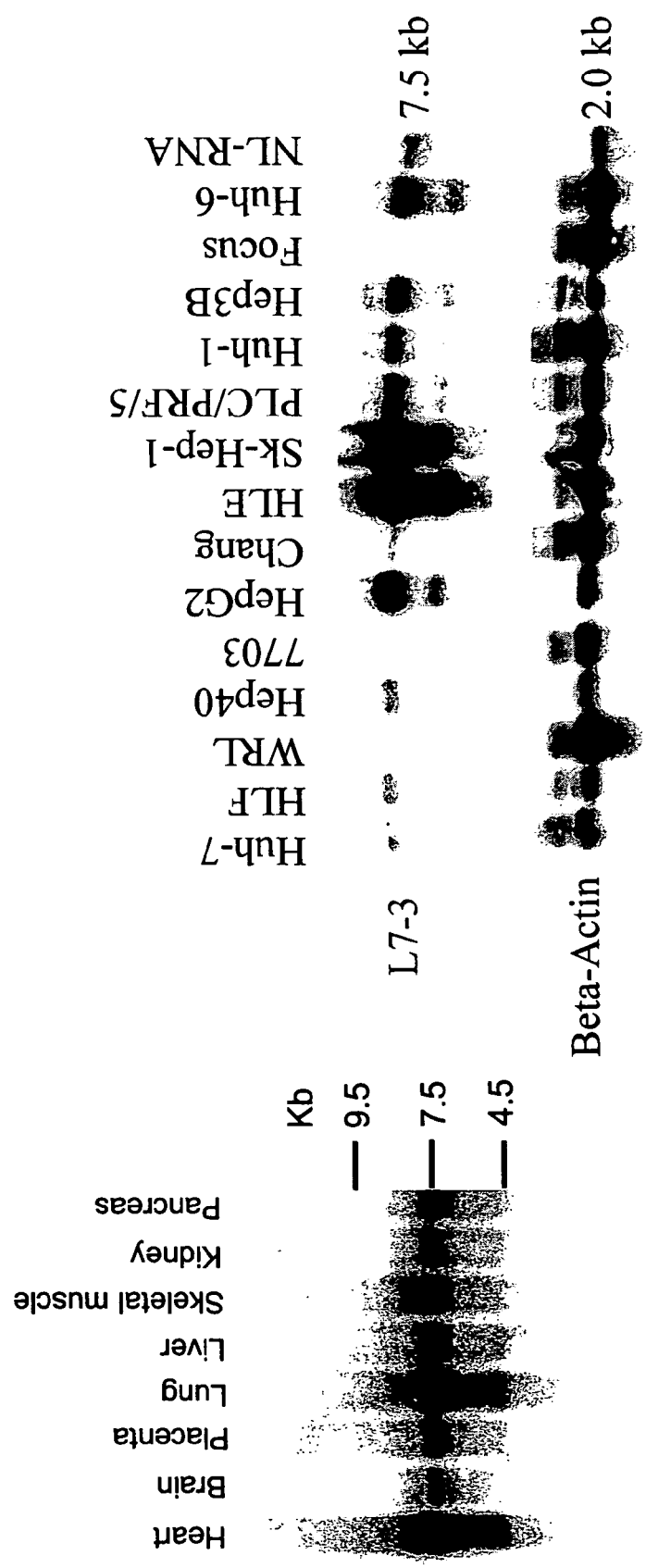

```
                           SEQUENCE LISTING

<160> NUMBER OF SEQ ID NOS: 31

<210> SEQ ID NO 1
<211> LENGTH: 3850
<212> TYPE: DNA
<213> ORGANISM: Homo sapiens
<220> FEATURE:
<221> NAME/KEY: CDS
<222> LOCATION: (325)..(3600)

<400> SEQUENCE: 1
tatgggctcg agcggccgcc cgggcaggtg cccgagcgag ggcgcttcgc tcccagccag      60
gacatggccg cacctctccg catcaggagc gccggctcac ggacttctcg cccaactccc     120
tgagcgctcc ctcgtttcga tctttagaaa accccgcttt ctttctgggg ccgtgacgag     180
gggcagggag cggcgagcaa ggatgcgttg aggaccgcga gggcgcgcgt ctcgggtgcc     240
gccgtgggtc ccgacgcgga agccgagccg cctccgcctg cctcgacttc cccacagcgc     300
ttccgccgcc gcctgccgtg cttg atg tgc aga aag aag ccg gac acc atg        351
                              Met Cys Arg Lys Lys Pro Asp Thr Met
                                1               5 atc cta aca caa att gaa gcc aag gaa gct tgt gat tgg cta cgg gca       399
Ile Leu Thr Gln Ile Glu Ala Lys Glu Ala Cys Asp Trp Leu Arg Ala
 10              15                  20                  25 act ggt ttc ccc cag tat gca cag ctt tat gaa gat ttc ctg ttc ccc       447
Thr Gly Phe Pro Gln Tyr Ala Gln Leu Tyr Glu Asp Phe Leu Phe Pro
             30                  35                  40 atc gat att tcc ttg gtc aag aga gag cat gat ttt ttg gac aga gat       495
Ile Asp Ile Ser Leu Val Lys Arg Glu His Asp Phe Leu Asp Arg Asp
         45                  50                  55
```

-continued

| | |
|---|---|
| gcc att gag gct cta tgc agg cgt cta aat act tta aac aaa tgt gcg<br>Ala Ile Glu Ala Leu Cys Arg Arg Leu Asn Thr Leu Asn Lys Cys Ala<br>     60                      65                      70 | 543 |
| gtg atg aag cta gaa att agt cct cat cgg aaa cga agt gac gat tca<br>Val Met Lys Leu Glu Ile Ser Pro His Arg Lys Arg Ser Asp Asp Ser<br>75                      80                      85 | 591 |
| gac gag gat gag cct tgt gcc atc agt ggc aaa tgg act ttc caa agg<br>Asp Glu Asp Glu Pro Cys Ala Ile Ser Gly Lys Trp Thr Phe Gln Arg<br>90                      95                    100                105 | 639 |
| gac agc aag agg tgg tcc cgg ctt gaa gag ttt gat gtc ttt tct cca<br>Asp Ser Lys Arg Trp Ser Arg Leu Glu Glu Phe Asp Val Phe Ser Pro<br>           110                    115                    120 | 687 |
| aaa caa gac ctg gtc cct ggg tcc cca gac gac tcc cac ccg aag gac<br>Lys Gln Asp Leu Val Pro Gly Ser Pro Asp Asp Ser His Pro Lys Asp<br>           125                    130                    135 | 735 |
| ggc ccc agc ccc gga ggc acg ctg atg gac ctc agc gag cgc cag gag<br>Gly Pro Ser Pro Gly Gly Thr Leu Met Asp Leu Ser Glu Arg Gln Glu<br>           140                    145                    150 | 783 |
| gtg tct tcc gtc cgc agc ctc agc agc act ggc agc ctc ccc agc cac<br>Val Ser Ser Val Arg Ser Leu Ser Ser Thr Gly Ser Leu Pro Ser His<br>           155                    160                    165 | 831 |
| gcg ccc ccc agc gag gat gct gcc acc ccc cgg act aac tcc gtc atc<br>Ala Pro Pro Ser Glu Asp Ala Ala Thr Pro Arg Thr Asn Ser Val Ile<br>170                      175                    180                185 | 879 |
| agc gtt tgc tcc tcc agc aac ttg gca ggc aat gac gac tct ttc ggc<br>Ser Val Cys Ser Ser Ser Asn Leu Ala Gly Asn Asp Asp Ser Phe Gly<br>                  190                    195                    200 | 927 |
| agc ctg ccc tct ccc aag gaa ctg tcc agc ttc agc ttc agc atg aaa<br>Ser Leu Pro Ser Pro Lys Glu Leu Ser Ser Phe Ser Phe Ser Met Lys<br>           205                    210                    215 | 975 |
| ggc cac gaa aaa act gcc aag tcc aag acg cgc agt ctg ctg aaa cgg<br>Gly His Glu Lys Thr Ala Lys Ser Lys Thr Arg Ser Leu Leu Lys Arg<br>           220                    225                    230 | 1023 |
| atg gag agc ctg aag ctc aag agc tcc cat cac agc aag cac aaa gcg<br>Met Glu Ser Leu Lys Leu Lys Ser Ser His His Ser Lys His Lys Ala<br>           235                    240                    245 | 1071 |
| ccc tca aag ctg ggg ttg atc atc agc ggg ccc atc ttg caa gag ggg<br>Pro Ser Lys Leu Gly Leu Ile Ile Ser Gly Pro Ile Leu Gln Glu Gly<br>250                      255                    260                265 | 1119 |
| atg gat gag gag aag ctg aag cag ctc agc tgc gtg gag atc tcc gcc<br>Met Asp Glu Glu Lys Leu Lys Gln Leu Ser Cys Val Glu Ile Ser Ala<br>                  270                    275                    280 | 1167 |
| ctc aat ggc aac cgc atc aac gtc ccc atg gta cga aag agg agc gtt<br>Leu Asn Gly Asn Arg Ile Asn Val Pro Met Val Arg Lys Arg Ser Val<br>           285                    290                    295 | 1215 |
| tcc aac tcc acg cag acc agc agc agc agc cag tcg gag acc agc<br>Ser Asn Ser Thr Gln Thr Ser Ser Ser Ser Gln Ser Glu Thr Ser<br>           300                    305                    310 | 1263 |
| agc gcg gtc agc acg ccc agc cct gtt acg agg acc cgg agc ctc agt<br>Ser Ala Val Ser Thr Pro Ser Pro Val Thr Arg Thr Arg Ser Leu Ser<br>315                      320                    325 | 1311 |
| gcg tgc aac aag cgg gtg ggc atg tac tta gag ggc ttc gat cct ttc<br>Ala Cys Asn Lys Arg Val Gly Met Tyr Leu Glu Gly Phe Asp Pro Phe<br>330                      335                    340                345 | 1359 |
| aat cag tca aca ttt aac aac gtg gtg gag cag aac ttt aag aac cgc<br>Asn Gln Ser Thr Phe Asn Asn Val Val Glu Gln Asn Phe Lys Asn Arg<br>           350                    355                    360 | 1407 |
| gag agc tac cca gag gac acg gtg ttc tac atc cct gaa gat cac aag<br>Glu Ser Tyr Pro Glu Asp Thr Val Phe Tyr Ile Pro Glu Asp His Lys | 1455 |

-continued

```
                365                 370                 375
cct ggc act ttc ccc aaa gct ctc acc aat ggc agt ttc tcc ccc tcg    1503
Pro Gly Thr Phe Pro Lys Ala Leu Thr Asn Gly Ser Phe Ser Pro Ser
        380                 385                 390 ggg aat aac ggc tct gtg aac tgg agg acg gga agc ttc cac ggc cct    1551
Gly Asn Asn Gly Ser Val Asn Trp Arg Thr Gly Ser Phe His Gly Pro
395                 400                 405 ggc cac atc agc ctc agg agg gaa aac agt agc gac agc ccc aag gaa    1599
Gly His Ile Ser Leu Arg Arg Glu Asn Ser Ser Asp Ser Pro Lys Glu
410                 415                 420                 425 ctg aag aga cgc aat tct tcc agc tcc atg agc agc cgc ctg agc atc    1647
Leu Lys Arg Arg Asn Ser Ser Ser Met Ser Ser Arg Leu Ser Ile
                430                 435                 440 tac gac aac gtg ccg ggc tcc atc ctc tac tcc agt tca ggg gac ctg    1695
Tyr Asp Asn Val Pro Gly Ser Ile Leu Tyr Ser Ser Ser Gly Asp Leu
            445                 450                 455 gcg gat ctg gag aac gag gac atc ttc ccc gag ctg gac gac atc ctc    1743
Ala Asp Leu Glu Asn Glu Asp Ile Phe Pro Glu Leu Asp Asp Ile Leu
        460                 465                 470 tac cac gtg aag ggg atg cag cgg ata gtc aat cag tgg tcg gag aag    1791
Tyr His Val Lys Gly Met Gln Arg Ile Val Asn Gln Trp Ser Glu Lys
    475                 480                 485 ttt tct gat gag gga gat tcg gac tca gcc ctg gac tcg gtc tct ccc    1839
Phe Ser Asp Glu Gly Asp Ser Asp Ser Ala Leu Asp Ser Val Ser Pro
490                 495                 500                 505 tgc ccg tcc tct cca aaa cag ata cac ctg gat gtg gac aac gac cga    1887
Cys Pro Ser Ser Pro Lys Gln Ile His Leu Asp Val Asp Asn Asp Arg
                510                 515                 520 acc aca ccc agc gac ctg gac agc aca ggc aac tcc ctg aat gaa ccg    1935
Thr Thr Pro Ser Asp Leu Asp Ser Thr Gly Asn Ser Leu Asn Glu Pro
            525                 530                 535 gaa gag ccc tcc gag atc ccg gaa aga agg gat tct ggg gtt ggg gct    1983
Glu Glu Pro Ser Glu Ile Pro Glu Arg Arg Asp Ser Gly Val Gly Ala
        540                 545                 550 tcc cta acc agg tcc aac agg cac cga ctg aga tgg cac agt ttc cag    2031
Ser Leu Thr Arg Ser Asn Arg His Arg Leu Arg Trp His Ser Phe Gln
    555                 560                 565 agc tca cat cgg cca agc ctc aac tct gta tca cta cag att aac tgc    2079
Ser Ser His Arg Pro Ser Leu Asn Ser Val Ser Leu Gln Ile Asn Cys
570                 575                 580                 585 cag tct gtg gcc cag atg aac ctg ctg cag aaa tac tca ctc cta aag    2127
Gln Ser Val Ala Gln Met Asn Leu Leu Gln Lys Tyr Ser Leu Leu Lys
                590                 595                 600 cta acg gcc ctg ctg gag aaa tac aca cct tct aac aag cat ggt ttt    2175
Leu Thr Ala Leu Leu Glu Lys Tyr Thr Pro Ser Asn Lys His Gly Phe
            605                 610                 615 agc tgg gcc gtg ccc aag ttc atg aag agg atc aag gtt cca gac tac    2223
Ser Trp Ala Val Pro Lys Phe Met Lys Arg Ile Lys Val Pro Asp Tyr
        620                 625                 630 aag gac cgg agt gtg ttt ggg gtc cca ctg acg gtc aac gtg cag cgc    2271
Lys Asp Arg Ser Val Phe Gly Val Pro Leu Thr Val Asn Val Gln Arg
    635                 640                 645 aca gga caa ccg ttg cct cag agc atc cag cag gcc atg cga tac ctc    2319
Thr Gly Gln Pro Leu Pro Gln Ser Ile Gln Gln Ala Met Arg Tyr Leu
650                 655                 660                 665 cgg aac cat tgt ttg gat cag gtt ggg ctc ttc aaa aaa tcg ggg gtc    2367
Arg Asn His Cys Leu Asp Gln Val Gly Leu Phe Lys Lys Ser Gly Val
                670                 675                 680 aag tcc cgg att cag gct ctg cgc cag atg aat gaa ggt gcc ata gac    2415
```

```
              Lys Ser Arg Ile Gln Ala Leu Arg Gln Met Asn Glu Gly Ala Ile Asp
                              685                 690                 695 tgt gtc aac tac gaa gga cag tct gct tat gac gtg gca gac atg ctg            2463
Cys Val Asn Tyr Glu Gly Gln Ser Ala Tyr Asp Val Ala Asp Met Leu
            700                 705                 710 aag cag tat ttt cga gat ctt cct gag cca cta atg acg aac aaa ctc            2511
Lys Gln Tyr Phe Arg Asp Leu Pro Glu Pro Leu Met Thr Asn Lys Leu
            715                 720                 725 tcg gaa acc ttt cta cag atc tac caa tat gtg ccc aag gac cag cgc            2559
Ser Glu Thr Phe Leu Gln Ile Tyr Gln Tyr Val Pro Lys Asp Gln Arg
730                 735                 740                 745 ctg cag gcc atc aag gct gcc atc atg ctg ctg cct gac gag aac cgg            2607
Leu Gln Ala Ile Lys Ala Ala Ile Met Leu Leu Pro Asp Glu Asn Arg
                750                 755                 760 gtg gtt ctg cag acc ctg ctt tat ttc ctg tgc gat gtc aca gca gcc            2655
Val Val Leu Gln Thr Leu Leu Tyr Phe Leu Cys Asp Val Thr Ala Ala
                765                 770                 775 gta aaa gaa aac cag atg acc cca acc aac ctg gcc gtg tgc tta gcg            2703
Val Lys Glu Asn Gln Met Thr Pro Thr Asn Leu Ala Val Cys Leu Ala
            780                 785                 790 cct tcc ctc ttc cat ctc aac acc ctg aag aga gag aat tcc tct ccc            2751
Pro Ser Leu Phe His Leu Asn Thr Leu Lys Arg Glu Asn Ser Ser Pro
    795                 800                 805 agg gta atg caa aga aaa caa agt ttg ggc aaa cca gat cag aaa gat            2799
Arg Val Met Gln Arg Lys Gln Ser Leu Gly Lys Pro Asp Gln Lys Asp
810                 815                 820                 825 ttg aat gaa aac cta gct gcc act caa ggg ctg gcc cat atg atc gcc            2847
Leu Asn Glu Asn Leu Ala Ala Thr Gln Gly Leu Ala His Met Ile Ala
                830                 835                 840 gag tgc aag aag ctt ttc cag gtt ccc gag gaa atg agc cga tgt cgt            2895
Glu Cys Lys Lys Leu Phe Gln Val Pro Glu Glu Met Ser Arg Cys Arg
                845                 850                 855 aat tcc tat acc gaa caa gag ctg aag ccc ctc act ctg gaa gca ctc            2943
Asn Ser Tyr Thr Glu Gln Glu Leu Lys Pro Leu Thr Leu Glu Ala Leu
            860                 865                 870 ggg cac ctg ggt aat gat gac tca gct gac tac caa cac ttc ctc cag            2991
Gly His Leu Gly Asn Asp Asp Ser Ala Asp Tyr Gln His Phe Leu Gln
    875                 880                 885 gac tgt gtg gat ggc ctg ttt aaa gaa gtc aaa gag aag ttt aaa ggc            3039
Asp Cys Val Asp Gly Leu Phe Lys Glu Val Lys Glu Lys Phe Lys Gly
890                 895                 900                 905 tgg gtc agc tac tcc act tcg gag cag gct gag ctg tcc tat aag aag            3087
Trp Val Ser Tyr Ser Thr Ser Glu Gln Ala Glu Leu Ser Tyr Lys Lys
                910                 915                 920 gtg agc gaa gga ccc cgt ctg agg ctt tgg agg tca gtc att gaa gtc            3135
Val Ser Glu Gly Pro Arg Leu Arg Leu Trp Arg Ser Val Ile Glu Val
                925                 930                 935 cct gct gtg cca gag gaa atc tta aag cgc cta ctt aaa gaa cag cac            3183
Pro Ala Val Pro Glu Glu Ile Leu Lys Arg Leu Leu Lys Glu Gln His
            940                 945                 950 ctc tgg gat gta gac ctg ttg gat tca aaa gtg atc gaa att ctg gac            3231
Leu Trp Asp Val Asp Leu Leu Asp Ser Lys Val Ile Glu Ile Leu Asp
    955                 960                 965 agc caa act gaa att tac cag tat gtc caa aac agt atg gca cct cat            3279
Ser Gln Thr Glu Ile Tyr Gln Tyr Val Gln Asn Ser Met Ala Pro His
970                 975                 980                 985 cct gct cga gac tac gtt gtt tta aga acc tgg agg act aat tta ccc            3327
Pro Ala Arg Asp Tyr Val Val Leu Arg Thr Trp Arg Thr Asn Leu Pro
                990                 995                 1000
```

```
aaa gga gcc tgt gcc ctt tta cta acc tct gtg gat cac gat cgc gca    3375
Lys Gly Ala Cys Ala Leu Leu Leu Thr Ser Val Asp His Asp Arg Ala
        1005                1010                1015 cct gtg gtg ggt gtg agg gtt aat gtg ctc ttg tcc agg tat ttg att    3423
Pro Val Val Gly Val Arg Val Asn Val Leu Leu Ser Arg Tyr Leu Ile
    1020                1025                1030 gaa ccc tgt ggg cca gga aaa tcc aaa ctc acc tac atg tgc aga gtt    3471
Glu Pro Cys Gly Pro Gly Lys Ser Lys Leu Thr Tyr Met Cys Arg Val
1035                1040                1045 gac tta agg ggc cac atg cca gaa tgg tac aca aaa tct ttt gga cat    3519
Asp Leu Arg Gly His Met Pro Glu Trp Tyr Thr Lys Ser Phe Gly His
1050                1055                1060                1065 ttg tgt gca gct gaa gtt gta aag atc cgg gat tcc ttc agt aac cag    3567
Leu Cys Ala Ala Glu Val Val Lys Ile Arg Asp Ser Phe Ser Asn Gln
            1070                1075                1080 aac act gaa acc aaa gac acc aaa tct agg tga tcactgaagc aacgcaaccg  3620
Asn Thr Glu Thr Lys Asp Thr Lys Ser Arg
        1085                1090 cttccaccac catggtgttt gttttttagaa gttttgccag tccttgaaga atgggttctg   3680
tgtgtaatcc tgaaacaaag aaaactacaa gctggagtgt aggaattgac tatagcaatt   3740
tgatacattt ttaaagctgc ttcctgtttg ttgagggtct gtattcatag accttgactg   3800
gaatatgtaa gactgtgcga aaaaaaaaaa aaaaaaaaa aaaaaaaaa              3850

<210> SEQ ID NO 2
<211> LENGTH: 1091
<212> TYPE: PRT
<213> ORGANISM: Homo sapiens

<400> SEQUENCE: 2

Met Cys Arg Lys Lys Pro Asp Thr Met Ile Leu Thr Gln Ile Glu Ala
 1               5                  10                  15

Lys Glu Ala Cys Asp Trp Leu Arg Ala Thr Gly Phe Pro Gln Tyr Ala
             20                  25                  30

Gln Leu Tyr Glu Asp Phe Leu Phe Pro Ile Asp Ile Ser Leu Val Lys
         35                  40                  45

Arg Glu His Asp Phe Leu Asp Arg Asp Ala Ile Glu Ala Leu Cys Arg
     50                  55                  60

Arg Leu Asn Thr Leu Asn Lys Cys Ala Val Met Lys Leu Glu Ile Ser
 65                  70                  75                  80

Pro His Arg Lys Arg Ser Asp Asp Ser Asp Glu Asp Glu Pro Cys Ala
                 85                  90                  95

Ile Ser Gly Lys Trp Thr Phe Gln Arg Asp Ser Lys Arg Trp Ser Arg
            100                 105                 110

Leu Glu Glu Phe Asp Val Phe Ser Pro Lys Gln Asp Leu Val Pro Gly
        115                 120                 125

Ser Pro Asp Asp Ser His Pro Lys Asp Gly Ser Pro Gly Gly Thr
    130                 135                 140

Leu Met Asp Leu Ser Glu Arg Gln Glu Val Ser Ser Val Arg Ser Leu
145                 150                 155                 160

Ser Ser Thr Gly Ser Leu Pro Ser His Ala Pro Ser Glu Asp Ala
                165                 170                 175

Ala Thr Pro Arg Thr Asn Ser Val Ile Ser Val Cys Ser Ser Ser Asn
            180                 185                 190

Leu Ala Gly Asn Asp Asp Ser Phe Gly Ser Leu Pro Ser Pro Lys Glu
        195                 200                 205
```

-continued

```
Leu Ser Ser Phe Ser Phe Ser Met Lys Gly His Glu Lys Thr Ala Lys
    210                 215                 220

Ser Lys Thr Arg Ser Leu Leu Lys Arg Met Glu Ser Leu Lys Leu Lys
225                 230                 235                 240

Ser Ser His His Ser Lys His Lys Ala Pro Ser Lys Leu Gly Leu Ile
                245                 250                 255

Ile Ser Gly Pro Ile Leu Gln Glu Gly Met Asp Glu Glu Lys Leu Lys
        260                 265                 270

Gln Leu Ser Cys Val Glu Ile Ser Ala Leu Asn Gly Asn Arg Ile Asn
            275                 280                 285

Val Pro Met Val Arg Lys Arg Ser Val Ser Asn Ser Thr Gln Thr Ser
    290                 295                 300

Ser Ser Ser Ser Gln Ser Glu Thr Ser Ser Ala Val Ser Thr Pro Ser
305                 310                 315                 320

Pro Val Thr Arg Thr Arg Ser Leu Ser Ala Cys Asn Lys Arg Val Gly
                325                 330                 335

Met Tyr Leu Glu Gly Phe Asp Pro Phe Asn Gln Ser Thr Phe Asn Asn
        340                 345                 350

Val Val Glu Gln Asn Phe Lys Asn Arg Glu Ser Tyr Pro Glu Asp Thr
            355                 360                 365

Val Phe Tyr Ile Pro Glu Asp His Lys Pro Gly Thr Phe Pro Lys Ala
    370                 375                 380

Leu Thr Asn Gly Ser Phe Ser Pro Ser Gly Asn Asn Gly Ser Val Asn
385                 390                 395                 400

Trp Arg Thr Gly Ser Phe His Gly Pro Gly His Ile Ser Leu Arg Arg
                405                 410                 415

Glu Asn Ser Ser Asp Ser Pro Lys Glu Leu Lys Arg Arg Asn Ser Ser
        420                 425                 430

Ser Ser Met Ser Ser Arg Leu Ser Ile Tyr Asp Asn Val Pro Gly Ser
            435                 440                 445

Ile Leu Tyr Ser Ser Ser Gly Asp Leu Ala Asp Leu Glu Asn Glu Asp
    450                 455                 460

Ile Phe Pro Glu Leu Asp Asp Ile Leu Tyr His Val Lys Gly Met Gln
465                 470                 475                 480

Arg Ile Val Asn Gln Trp Ser Glu Lys Phe Ser Asp Glu Gly Asp Ser
                485                 490                 495

Asp Ser Ala Leu Asp Ser Val Ser Pro Cys Pro Ser Ser Pro Lys Gln
        500                 505                 510

Ile His Leu Asp Val Asp Asn Asp Arg Thr Thr Pro Ser Asp Leu Asp
    515                 520                 525

Ser Thr Gly Asn Ser Leu Asn Glu Pro Glu Pro Ser Glu Ile Pro
530                 535                 540

Glu Arg Arg Asp Ser Gly Val Gly Ala Ser Leu Thr Arg Ser Asn Arg
545                 550                 555                 560

His Arg Leu Arg Trp His Ser Phe Gln Ser Ser His Arg Pro Ser Leu
                565                 570                 575

Asn Ser Val Ser Leu Gln Ile Asn Cys Gln Ser Val Ala Gln Met Asn
        580                 585                 590

Leu Leu Gln Lys Tyr Ser Leu Leu Lys Leu Thr Ala Leu Leu Glu Lys
            595                 600                 605

Tyr Thr Pro Ser Asn Lys His Gly Phe Ser Trp Ala Val Pro Lys Phe
    610                 615                 620

Met Lys Arg Ile Lys Val Pro Asp Tyr Lys Asp Arg Ser Val Phe Gly
```

-continued

```
            625                 630                 635                 640
Val Pro Leu Thr Val Asn Val Gln Arg Thr Gly Gln Pro Leu Pro Gln
                    645                 650                 655
Ser Ile Gln Gln Ala Met Arg Tyr Leu Arg Asn His Cys Leu Asp Gln
                    660                 665                 670
Val Gly Leu Phe Lys Lys Ser Gly Val Lys Ser Arg Ile Gln Ala Leu
                    675                 680                 685
Arg Gln Met Asn Glu Gly Ala Ile Asp Cys Val Asn Tyr Glu Gly Gln
                    690                 695                 700
Ser Ala Tyr Asp Val Ala Asp Met Leu Lys Gln Tyr Phe Arg Asp Leu
705                 710                 715                 720
Pro Glu Pro Leu Met Thr Asn Lys Leu Ser Glu Thr Phe Leu Gln Ile
                    725                 730                 735
Tyr Gln Tyr Val Pro Lys Asp Gln Arg Leu Gln Ala Ile Lys Ala Ala
                    740                 745                 750
Ile Met Leu Leu Pro Asp Glu Asn Arg Val Val Leu Gln Thr Leu Leu
                    755                 760                 765
Tyr Phe Leu Cys Asp Val Thr Ala Ala Val Lys Glu Asn Gln Met Thr
                    770                 775                 780
Pro Thr Asn Leu Ala Val Cys Leu Ala Pro Ser Leu Phe His Leu Asn
785                 790                 795                 800
Thr Leu Lys Arg Glu Asn Ser Ser Pro Arg Val Met Gln Arg Lys Gln
                    805                 810                 815
Ser Leu Gly Lys Pro Asp Gln Lys Asp Leu Asn Glu Asn Leu Ala Ala
                    820                 825                 830
Thr Gln Gly Leu Ala His Met Ile Ala Glu Cys Lys Lys Leu Phe Gln
                    835                 840                 845
Val Pro Glu Glu Met Ser Arg Cys Arg Asn Ser Tyr Thr Glu Gln Glu
                    850                 855                 860
Leu Lys Pro Leu Thr Leu Glu Ala Leu Gly His Leu Gly Asn Asp Asp
865                 870                 875                 880
Ser Ala Asp Tyr Gln His Phe Leu Gln Asp Cys Val Asp Gly Leu Phe
                    885                 890                 895
Lys Glu Val Lys Glu Lys Phe Lys Gly Trp Val Ser Tyr Ser Thr Ser
                    900                 905                 910
Glu Gln Ala Glu Leu Ser Tyr Lys Lys Val Ser Glu Gly Pro Arg Leu
                    915                 920                 925
Arg Leu Trp Arg Ser Val Ile Glu Val Pro Ala Val Pro Glu Glu Ile
                    930                 935                 940
Leu Lys Arg Leu Leu Lys Glu Gln His Leu Trp Asp Val Asp Leu Leu
945                 950                 955                 960
Asp Ser Lys Val Ile Glu Ile Leu Asp Ser Gln Thr Glu Ile Tyr Gln
                    965                 970                 975
Tyr Val Gln Asn Ser Met Ala Pro His Pro Ala Arg Asp Tyr Val Val
                    980                 985                 990
Leu Arg Thr Trp Arg Thr Asn Leu Pro Lys Gly Ala Cys Ala Leu Leu
                    995                 1000                1005
Leu Thr Ser Val Asp His Asp Arg Ala Pro Val Val Gly Val Arg Val
        1010                1015                1020
Asn Val Leu Leu Ser Arg Tyr Leu Ile Glu Pro Cys Gly Pro Gly Lys
1025                1030                1035                1040
Ser Lys Leu Thr Tyr Met Cys Arg Val Asp Leu Arg Gly His Met Pro
                    1045                1050                1055
```

```
Glu Trp Tyr Thr Lys Ser Phe Gly His Leu Cys Ala Ala Glu Val Val
        1060                1065                1070

Lys Ile Arg Asp Ser Phe Ser Asn Gln Asn Thr Glu Thr Lys Asp Thr
    1075                1080                1085

Lys Ser Arg
   1090

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 3
tatgggctcg agcggccgcc c                                           21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 4
cgcacagtct tacatattcc a                                           21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 5
atgtgcagaa agaagccgga cacc                                        24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 6
cctagatttg gtgtctttgg tttc                                        24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 7
gacaccacca tctctgtgct c                                           21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 8
```
gcagactgtc cttcgtagtt g          21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 9
cactccggtc cttgtagtct ggaacc          26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 10
atcctcttca tgaactcggg cacgg          25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 11
gatcaaggtt ctagactaca aggaccg          27

<210> SEQ ID NO 12
<211> LENGTH: 691
<212> TYPE: DNA
<213> ORGANISM: Artificial Sequence
<220> FEATURE:
<223> OTHER INFORMATION: Description of Artificial Sequence: probe
<220> FEATURE:
<221> NAME/KEY: misc_feature
<222> LOCATION: (1)..(691)
<223> OTHER INFORMATION: n represents a or g or c or t/u

<400> SEQUENCE: 12
ccngcaganc tcgaaaatat gcttcggcat gtctgccacg tcataagcag actgtccttc     60
gtagttgaca cagtctatgg caccctcatt catctggcgc agagcctgaa tccgggactt    120
gaccccccgat tttctgaaga gcccaacctg tcggaagagc aacactaagt gtggggtaca    180
ttcacgtgga cgcagtgttt acaccacaca actagaagaa gctgcatgta atccgagctc    240
ccctgagtac gtgaacccgc aggcagcgct ctcacctgat ccaaacaatg gttccggggg    300
tatcgcacgg cctgctggat gctctcaggc aacggttgtc ctgtgcgctg cacgttgacc    360
gtcaggggac cccaaacaca ctccggtcct tgtagtctgg aaccttgatc ctcttcatga    420
actcgggcac ggccctgtta aagagcacag agatggtggt gtcggcggan acatgctcac    480
ttgtctgtct acacttgtcc aattctgcag gcaaaccctg tgggctccag attctgatat    540
catccaatga attcgagctc gtaccgggga tcctctaaaa tccaacttgc aggcattcca    600
gcttcagctg ctccaatttc tatatgttcc cctaaatcgt attttttga aacataaggt    660
tatttttta attgtaccnc gttcctaacn a                                    691

<210> SEQ ID NO 13

```
<211> LENGTH: 301
<212> TYPE: DNA
<213> ORGANISM: Artificial Sequence
<220> FEATURE:
<223> OTHER INFORMATION: Description of Artificial Sequence: probe

<400> SEQUENCE: 13
gaggctctat gcaggcgtct aaatacttta acaaatgtg cggtgatgaa gctagaaatt      60
agtcctcatc ggaaacgaag tgacgattca gacgaggatg agccttgtgc catcagtggc    120
aaatggactt ccaaaggga cagcaagagg tggtcccggc ttgaagagtt tgatgtcttt    180
tctccaaaac aagacctggt ccctgggtcc cagacgact cccacccgaa ggacggcccc    240
agccccggag gcacgctgat ggacctcagc gagcgccagg aggtgtcttc cgtccgcagc    300
c                                                                   301

<210> SEQ ID NO 14
<211> LENGTH: 3006
<212> TYPE: DNA
<213> ORGANISM: Homo sapiens
<220> FEATURE:
<221> NAME/KEY: misc_feature
<222> LOCATION: (1)..(3006)
<223> OTHER INFORMATION: n represents a or g or c or t/u

<400> SEQUENCE: 14
cnggcagatc tcgaanatac tgcttcggca tgtctgccac gtcataagca gactgtcctt      60
cgtagttgac acagtctatg gcaccytcat tcatctggcg cagagcctga atccgggact    120 tgaccccga ttttctgaag agcccaacct gtcggaagag caacactaag tgtggggtac     180
attcacgtgg acgcagtgtt tacaccacac aactagaaga agctgcatgt aatccgagct    240
cccctgagta cgtggacccg caggcagcgc tctcacctga tccaaacaat ggttccggrg    300
gtatcgcayg gcctgctgga tgctctgagg caacggttgt cctgtgcgct gcacgttgac    360
cgtcagtggg accccaaaca cactccggtc cttgtagtct ggaaccttga tcctcttcat    420
gaacttgggc acggcctgtt aaagaacaca gagatggtgg tgttggcgga gacatgctca    480
cttgtctgtc tacacttgtc caattctgca ggcaaaccct gtgggctcca gatctgtgct    540
aatacggtgg ctacttaaat ttaaattaaa caaaatgaca aattcagttc cccagtggta    600
ctggccacac ttcaggtgct ccttcatctt ttgtgctcag tacctactgt attggcctgt    660
gcagataaag aacattccta tcatccgac agttctcctg gacagtgctg ttctagatct    720
tctaagagtg ggggttgaca ggtccgtttc ctcagttagg agcgtccttc caccttgaac    780
ctggagaatt ggggtctaca gtcttaagga agctgatgga tttccttaca gaatggcggt    840
ataggatgga acaagcagaa aacaaacatgt aatacccctaa ttaggtgcat ctgatagagt    900
gtgaaaaaca aggtcccttt tgtcttgaaa aagggtaag aatcacttct gagttcttga     960
tgagatcgaa agcatttagg gtcaaaaggc gcagataaca catgatggga aaacagcaat   1020
gagagcctaa cacaatggga gccaactcca gagctcaaca gtgaatgacc tgaagtcaaa   1080
ataaaatctg ctgctgatga cccggagaac attacatctt taggtttcta aaggaagatg   1140
gaaaaggaac aatgggggtt ttgtgagccg accccaggct ccctggtgtc ctgaaaccag   1200
gtccacccca gcactatatg caacagcagg aaacccatgt catgcatttc aggctgtcaa   1260
gcagaaattc cagctctcca aatgacctct ctgaacagga cccgaaaggg caaggccaaa   1320
caggaaaaga accttgtgta ggattcctcc ctgctccaca gatcccacca tgtgaggctt   1380
ttacagttgg ttttgagtca ctggaaacac tgaccagaac acaagaagta ttatggactt   1440
```

```
tcagattctt gagggtttgg tgggatggg ggtgggccac tccgaaatga gaatctaaaa   1500
tatgcagttt taaatagcca gcagggaaaa cattactcta agcacagagg aactccagag   1560
aagacagact gctttgcctt ttgaatgctc accagcagcc atggcatgtt actgtttata   1620
gctccaggaa aggtaaaacg aaagagcaaa gttaagtttg tatttccata cagttaagtg   1680
tgtggtatca tggctataag tgtgcataat actcgctttg tcggggaga aaagcccgac   1740 ggcggaatgt gaaaagaaca cattacgatc cccaccgaga atctgaagca tgtgaggata   1800
aaccggtcaa tacttatttc tgtcattcag aacaaacaac ttctgtattt agcaaggctc   1860
acataataac agcctttgaa cgggagtgct ttgatgctga agttaaatct gctatgatcc   1920
taaggagagg aggagctgga gacaaaaaga acagtttcct tgcttgccg actttctcaa   1980 gcaacttggg tttgctacag agtgctacta atgaaatggg cggcttctcc attttatca   2040 aatatggtag tgtgcgactg gataataaac actcagatta ctgaaaagac ttaaggattc   2100
ccagatgaca ctgaaaatg cactgagatg tcaatctaga aacatttctc tgcttggcac   2160
tgatagcaga aaaattaaga tgtacccaga ttaggtgata tccatgaccc atctagcctt   2220
acagcctacc cctcacattc tatatactaa ggagctatat ttttcaaagt aattatgaac   2280
aatttgtaca atgcattca tctctacatt tgagtctata atatgttaga gtagtgaatt   2340
ccttaaaata attattcact gttagacagt ctttgctaga aaaaagtaa cctgaattct   2400 ttagcacagg tggatgctac aaatayctgc mcrkscrrmy kywykakymy tattattatt   2460
attattattt tttgagatag agtcttactc tgtcacccag gctggagtgc agtagcctta   2520
tcttggggct cactgcaacc tccatcttct gggctcaagg gattctcatg cctcagcttc   2580
ctgagtagat gggattacag gtgcatgcca ccacactcag ctaattttg tattttagt   2640 agagaatggg gttcgccaat gttggccagc tggtctcaaa ctcctggcgt catgtgatcc   2700
acctatgtca gattcccaag atgctgggat acaggcatga ccacacacc cgccccaaga   2760 tgatttctaa aacaggcat gaatacggta taagaacagg twctgtaant caagnaattc   2820
caaganggtc tcaywawatc twatkgttgt ccttctcctc cayccagaaa tacratctgm   2880
tactgtgcat acattwactg awagtggawk atyctawtat tattgggaan ganccctat    2940 caccacntga ccctaagagt attgnatttt caccccntca tctggcgata tgacntgccc   3000 gngggg                                                              3006

<210> SEQ ID NO 15
<211> LENGTH: 305
<212> TYPE: DNA
<213> ORGANISM: Homo sapiens

<400> SEQUENCE: 15
tcaaaggcat gggaaatgat agattttatg catttgaact agcaaacaga tgtttctcat     60
tttatttcca tgctttctaa cttaaataat tcatcagctt ttctttcttt tctctgatag    120
gggccacatg ccagaatggt acacaaaatc ttttggacat ttgtgtgcag ctgaagttgt    180
aaagatccgg gattccttca gtaaccagaa cactgaaacc aaagacacca aatctaggtg    240
atcactgaag caacgcaacc gcttccacca ccatggtgtt tgtttctaga acttttgcca    300
gtcct                                                                305

<210> SEQ ID NO 16
<211> LENGTH: 466
<212> TYPE: DNA
```

```
<213> ORGANISM: Homo sapiens
<220> FEATURE:
<221> NAME/KEY: misc_feature
<222> LOCATION: (1)..(466)
<223> OTHER INFORMATION: n represents a or g or c or t/u

<400> SEQUENCE: 16
tggattnccn tgncactgaa aaatacatcc tctttccagg tgagcgaagg acccccctctg      60 aggctttgga ggtcagtcat tgaagtccct gctgtgccag aggaaatctt aaagcgccta     120
cttaaagaac agcacctctg ggatgtagac ctgttggatt caaaagtgat cgaaattctg     180
gacagccaaa ctgaaattta ccagtatgtc caaaacagta tggcacctca tcctgctcga     240
gactacgttg ttttaaggtg agcgcttccc agttgttttt tgtgacaag gatgactcca     300 tatatgaacc aagcctatat gtcactgatc ttacaagatg gtataattat ttaaagtaga     360
ggccgggcat atggtggctc acacctgtaa tcccagcact ctgggaggcc aaggtgggag     420
gatcacttga ggccagcagt tcaagaccag cctggntaat atagca                   466

<210> SEQ ID NO 17
<211> LENGTH: 692
<212> TYPE: DNA
<213> ORGANISM: Homo sapiens
<220> FEATURE:
<221> NAME/KEY: misc_feature
<222> LOCATION: (1)..(692)
<223> OTHER INFORMATION: n represents a or g or c or t/u

<400> SEQUENCE: 17
ccngcaganc tcgaaaatat gcttcggcat gtctgccacg tcataagcag actgtccttc      60
gtagttgaca cagtctatgg caccctcatt catctggcgc agancctgaa tccgggactt     120 gaccccccgat tttctgaaga gcccaacctg tcggaagagc aacactaagt gtggggtaca    180
ttcacgtgga cgcagtgttt acaccacaca actagaagaa gctgcatgta atccgagctc     240
ccctgagtac gtgaacccgc aggcagcgct ctcacctgat ccaaacaatg gttccggggg     300
tatcgcacgg cctgctggat gctctgaggc aacggttgtc ctgtgcgctg cacgttgacc     360
gtcaggggac cccaaacaca ctccggtcct tgtagtctgg aaccttgatc ctcttcatga     420
actcgggcac ggccctgtta aagagcacag agatggtggt gtcggcggan acatgctcac     480
ttgtctgtct acacttgtcc aattctgcag gcaaaccctg tgggctccag attctgatat     540
catccaatga attcnanctc ngtaccgggg atcctctaaa atccaacttg caggcattcc     600
agcttcagct gctccaattt ctatatgttc cctaaatcn tatttttttg aaacataagg     660 ttatttttt aattgtaccn cgttcctaac na                                    692

<210> SEQ ID NO 18
<211> LENGTH: 315
<212> TYPE: DNA
<213> ORGANISM: Homo sapiens
<220> FEATURE:
<221> NAME/KEY: misc_feature
<222> LOCATION: (314)
<223> OTHER INFORMATION: n represents a or g or c or t/u

<400> SEQUENCE: 18
tttcgtgtga ggggcttagc tcttgttcgg tataggaatt acgacatcgg ctcatttcct      60
cgggaacctg tgcggaacat gacagacaga aaggaggtga gtccacctgt actcaatctc     120 aatgccatc agtggaaaag actgggtagg aacaatggcc tggtccttaa agcagtgcag     180
gcatcttccc gccggaggtg ggctatcatg ctgaccgcac gtgttatcac gaggatatga     240
```

| | |
|---|---|
| acagatcacc tccataaatg tatctgaaat cttatttcca tgtaaggtct ttggaaagtt | 300 |
| agagtagggg gagnc | 315 |

<210> SEQ ID NO 19
<211> LENGTH: 281
<212> TYPE: DNA
<213> ORGANISM: Homo sapiens
<220> FEATURE:
<221> NAME/KEY: misc_feature
<222> LOCATION: (1)..(281)
<223> OTHER INFORMATION: n represents a or g or c or t/u

<400> SEQUENCE: 19

| | |
|---|---|
| ctcnngactg tgtggatggc ctgtttaaag aagtcaaaga gaagtttaaa ggctgggtca | 60 |
| ngctactcca cttcggagca ggctgagctg tcctataaga aggtaaggct tcaccctgtt | 120 |
| gtcggctagt tgagtccagg agtcgaagct tgggtccatc agagataaca cgcttttgcc | 180 |
| aactaatctg tctgggatc tgtagcccac aacctcccctt gtagagctgg gcaccggggt | 240 |
| gagtaagatc cccgtggtga gagtggaaac cgnncaaagc a | 281 |

<210> SEQ ID NO 20
<211> LENGTH: 1713
<212> TYPE: DNA
<213> ORGANISM: Mus musculus
<220> FEATURE:
<221> NAME/KEY: misc_feature
<222> LOCATION: (1)..(1713)
<223> OTHER INFORMATION: n represents a or g or c or t/u

<400> SEQUENCE: 20

| | |
|---|---|
| ttgaacgctt gggtaccggg ccccccctcg aggtcgacgg tatcgataag cttgatatcg | 60 |
| aattcctgca gcccggggga tccaatccct gggtccccag acaactctcg tttgcaaagc | 120 |
| gccacaagcc acgaaagcat gctgacagac ctcagcgagc accaggaggt ggcctctgtc | 180 |
| cgaagcctca gcagcaccag cagcagcgtc cccacccacg cagcccacag tggagatgcc | 240 |
| actacgcccc gaaccaattc cgtcatcagc gtctgctcct ccggacactt tgtaggcaac | 300 |
| gatgactctt tttccagcct gccgtctccc aaggaactgt ccagcttcag ttttagcatg | 360 |
| aaaggccacc acgagaagaa caccaagtcg aagacgcgga gcctgctcaa acgcatggag | 420 |
| agcctgaagc tcaagggctc ccaccacagc aagcacaagg cgccttccaa gctggggttg | 480 |
| atcatcagtg ctcccattct gcaggagggt atggatgagg cgaagctgaa gcagctgaac | 540 |
| tgtgtggaga tctcagccct caatggcaac acatcaacg tgcccatggt accggaaaag | 600 |
| gagccgtgtc taacttcacc cagaccagca gcaagcagca gccaatcaga gaccagcagc | 660 |
| gcggtcagca cacccagccc ggtcaccagg acccggagcc tcagcacctg taacaagcgg | 720 |
| gtgggcatgt atctagaggg cttcgaccca ttcagtcagt ccaccttgaa caacgtgacg | 780 |
| gagcagaact ataaaaaccg tgagagctac ccagaggaca cggtgttcta cattcccgaa | 840 |
| gatcacaagc ccggcacctt ccctaaggcc ctctcccatg gcagtttctg tcctcgggga | 900 |
| aacagttctg tgaactggag gaccggaagc ttccatggcc ccggccatct cagcctacgg | 960 |
| agagaaaaca gccatgacag tcctaaggag ctgaagagac gcaattcttc cagctctctg | 1020 |
| agcagccgcc tgagcatcta tgataacgta ccgggttcta tcctgtactc cagctcggga | 1080 |
| gaactggccg acctgagaa tgaggacatc ttccctgagc tggatgacat tctctaccac | 1140 |
| gtgaagggga tgcagcggat agtcaaccag tggtccgaga agtttccga cgagggagac | 1200 |

| | |
|---|---:|
| tcggactcag ccctggactc tgtctctcct tgcccgtcat cttcaaaaca gattcacctg | 1260 |
| gatgtggacc atgaccgaag gacacccagt gacctggaca gcacaggcaa ctccttcaat | 1320 |
| gagcccgaag agcccactga tatccggaaa aagagacttc ccggggtggg ggctttcctt | 1380 |
| gaccagtgca ataggtaagg gaaaggcgtt gctttctcgg atgcattcca aaaggtgggg | 1440 |
| gaaattcaaa gaaaggggtc ttgctttggg tggggattgg agttctngat anttttgcca | 1500 |
| agttccttgg aaaattcctt aggggaattg gatncccaac cngggaagaa cccccaaaca | 1560 |
| aatccccnaa cngggaaaaa ggnggttttt attnaaaacc tggggtnntt gaaacccttt | 1620 |
| gggccattca aangggattn ccntacccag gtggggancc cttggaaana aangggtggg | 1680 |
| tggttttgga aacnaatttt tagtcccngg gcc | 1713 |

<210> SEQ ID NO 21
<211> LENGTH: 4767
<212> TYPE: DNA
<213> ORGANISM: Mus musculus
<220> FEATURE:
<221> NAME/KEY: misc_feature
<222> LOCATION: (1)..(4767)
<223> OTHER INFORMATION: n represents a or g or c or t/u

<400> SEQUENCE: 21

| | |
|---|---:|
| cataccaagt gaggtgtaat tgtttaaacc aaaaagtttg aaggatatgg caaaagccag | 60 |
| acttaaattt ccattttttcc tttttttttt tttttttaag ggaaattctt attcaatgtg | 120 |
| taagtgctca ctatcatctc tggggaggca gaggagaaa aaaaataccct ggtaattcaa | 180 |
| agccagtctg ggctacacag caagatcgtc cctcaaaaaa gtactttta attaaaagag | 240 |
| agaaattatt ccgaatccat agaaatagtc gttgagtat tgggaggtgg gaagcccaag | 300 |
| gcccttgtcc atgtagtcac acataatggc agtggcttgg gctttcatag aagggcacac | 360 |
| gtggggacct tcccttgtgg gctttctgac tcttcactta ctgcatatgc ctactgcaga | 420 |
| gatttcctct ggactggagc actgggactt tcttctaaaa aatataaagt tcagtaatga | 480 |
| ccaacaatta tgattaggct agtaggcttt tgttcatttt taaaaattgt atgtgtgtga | 540 |
| gtattttacc tcacgcatag tgtatgtacc gtgcctctga agacggaaga aaacattagc | 600 |
| ttccccctgga actggagtta cagatggttg taagccacca tgtaagtgct gggatttgaa | 660 |
| ctcaggtcca tctggaagaa cagccagtgc ggtacccact gagccatctc tccagccccc | 720 |
| tgcccagtgt tcttaaagtg ttagtctacg gtagcagatg atttggtccc ttgaagaaat | 780 |
| tctttcccct caatcttgct agcttgactg ataacctaaa cccattgagg aagctctgat | 840 |
| cacgagcaag ctctactccg gactggaaga gtgttcagtg tgtctcaaag cacgtacttg | 900 |
| tggtgttgta accgtgagc catgctgaga cgcctcttgt gaaatgtctt cccgtggctt | 960 |
| caggaacatt tcagaccgct gttttccttt ggagttaaaa ctgactcctt ctaccaacac | 1020 |
| gtggaaagaa ttgtgaacat cagctggtag ttgtcatatg aaaaaacaaa acaaaacaaa | 1080 |
| acaaaaaact atgttgtctg tcactgtcat cttcagtatg tactttgtcc ccaaatcacc | 1140 |
| atgacatgcc aaagccgtgt caagcattgc agagacattc taaccttgtt gctcttacta | 1200 |
| ttcagtttaa aaagaagcaa gtaattgtgg gaaggtaggg gatgcttgga agaggacttt | 1260 |
| gctatgtaga ccaaactggg ctagaactca acaatcctcc tgcctcagcc tcccatgtgc | 1320 |
| tacatgcaac aaacaaggag cttaaacatt ttttttttttt atgaatgcca ggaaaaccta | 1380 |
| caggaatttg aagaatttt gtgggagcct ctgttttctt atttcttctt ctgtcttatt | 1440 |
| ttaaatgcaa gaaggggcag acctccacct gctctccttt tatctgtgcg cctccagccc | 1500 |

-continued

```
tagccccaac cttgtgctgc aaagctcttg aagcttcgac attgcacctt tggctccatc   1560
tgtcttgaaa aacggaccca aggcacccaa gagataagac ctgcacattc ctgctgggcc   1620
cttgccttgg gtggcggcgg ggtcagaatg cccaaggcca cagatggtta ctatagcgc    1680
tatctcggcc acctacttga acgatcctac ttcaggtcct cttggctggc ttttctatat   1740
tttcttttct tttctgccat tgttaatact tgtttcacaa ccaactgtag aggttgctgt   1800
ctttgggcac cagagccact gtgctttaat cctgggttct taggcaagat tcctaagctc   1860
tctaagcccc gcccccatcc cctttcgtcc cttataaaat aaagataaat catagtatct   1920
gtggcagaag gttgtcagag gactgaagac gagccagtgc agtgtcaccc aaagacagtg   1980
gcagttcacc tagttagaac catattttaa ttcttggttg acagagcacg actgtatgta   2040
tctatgtggt agcaagtgat gtttcaatgt ttgtgtgtaa ggtgaatgag tgaattatgg   2100
gggttaacat atccgatagc ttataggttt atcatcttgt ctggagtata tgcaaattgg   2160
ctattttaaa atataaaatt aatattaact atagtcaccc tggtatgcca agtcgccctg   2220
cacttgctgc ctgcctcttt gcgactccct gtcccttccc aacttctggt gaccatcctt   2280
ctgttcccct ctatgaaatg agtttcttct ctggtcagaa ctactatctt atgtccctag   2340
tacccctccg gaaatctgag ggtcctgctc tttggagatc ctagagcatg cggatgggtg   2400
aggggaaatc attgaaaaac cacagaaacc cagagaggaa gcggcacgcc cctagtctgg   2460
tgccaccagc ataaaaagtt aaagttgact tttctcaaac caacctcctg ggtcttttgt   2520
tgtttgactt aaactggcgt gtgtgaagtt actccacctc cccaagcccc ataggcctcc   2580
atgcctagta aatttggtta taaacaccac tcagccatta aagccccaat gcagtccagt   2640
ggagatttga ttacgggttc gattaatgaa tcccagacct aagactaact taaccattgc   2700
tcactcttaa agccttgaaa aaaactgggg gagtgaaaca ttacatttgg ttgtgtcctt   2760
taactgagac ccctcagcaa gggaccctac acccttctga gcctccagtg tctctcaact   2820
gttcctcctg ccctycccca ctcctccagt gtctctcaac tgttcctcct gccctccccc   2880
actccttttcc catgcaagga gaggtttttc tgaaagagtt ggtgttctgt tttatctcag   2940
tttattattc tataaacagg cttccacata atctatagaa tcaaaggcag gcttctcagg   3000
ctgcagagat actacctatc ctggtgcatc caagttgtca gagcaggacc cgggagataa   3060
agcccagcag ggtacaagat cagttccaag tggagggaat taagcggctc ttattccatg   3120
gaaaaaaaaa agcaaggttg caataattcg ggaaagaaat aaaagactga tgggtgtgtg   3180
tgtgtgtgtg tgtgtgtgtg tgtgtgtgtg tgtgtgtgta agcttatgag gcaacaagca   3240
gacgcattta aaaaggaaga ctttggtgat gatcatctgg aagattctag aaagaactga   3300
ggcccaggga cctgtcactc acactttgca tactaggtag cgagtagata acgggtgcta   3360
ctgttgtttt tgttttttt tttttctcct atgactttta atgaagctga ttgattgatg    3420
actgattgat cgattgattg attgatggtt gattgatcga ctgattgatt tccattgtgc   3480
taaggattga acttgaagcc ttgtgtgtcc ttcgcaagta cctgatcact gaactactct   3540
gccgtccccc tttctctaat gtggctaaac cgatatcatt ggcgatgggg gcaactcgtt   3600
caaagctgca gtttgactcc catctcagcg gggactgtgt tctaagggcc tgtttgtgct   3660
cagtgagatt tttaaaataa tcatttgtgc agttgctgtc gatactgaaa acagtctctc   3720
ctgataggac tgagtaataa agaggcctgg aacttcgcct ctgtataata aattcaagca   3780
ataaaagtca ccttctgaca tggacatttc tgaggcccat tgtccttctt aattattact   3840
```

```
tgagtgagaa gggtgcactg agcactttgc ctgcaacctt ccccagttcc tactgctggc     3900
ctgttgccct tgaagtgggc ctgccattga tgctgtagca tgccgtctaa caagaaatag     3960
aatggcactt ttgtgttaga caagcttttt tttttttttt tgagaataga actcactagc     4020
tagaccaggc tggcctccaa ctcacagaga cctacttgcc tctgccttct gggtattaag     4080
attaaagacg tgcactacca tcctgggact ccattacccg ctatgtaatt gaagtgtagc     4140
atacctgccg aaactagaaa tgagttccga gaagctcata ttgtatgggt cagttgttca     4200
gtttgattgc ccattcgtgg ttcctttctc tgctcacggc cttctctgc tctgcaggcg     4260 cttaaatact ctaaacaagt gtgcagtcat gaagctggag attagtcctc accggaagcg     4320
agtgagtacc aaaattacat gggggggggg ggcagggaca gcaggcacac taaccaagac     4380
aggacttgta tctacactct gtaaaaggcc ctgtttgtcc attcctcaac atgttaaaac     4440
ccctatttgg agacagtagt ggatggtggc atctactgct ctggacttga agaaatctgt     4500 tactttttccc agtgaactcc atggctacca tgtgattcaa agcatgaagc ctattgaatc     4560
tccagaggaa tttcacattg ctccctagag gaaataaagc taacattctg taggacctct     4620 tcctgttttcc tggatggaac agtagctcca tctcgaagct gtcaagatga aaggggaagg     4680
ctggcttggg ggatactgta ggagatgtgg atcgtggggg gtgggagga agacgccgga     4740 gcaggaaatc ccatacactc tgtggna                                         4767

<210> SEQ ID NO 22
<211> LENGTH: 1072
<212> TYPE: DNA
<213> ORGANISM: Mus musculus
<220> FEATURE:
<221> NAME/KEY: misc_feature
<222> LOCATION: (6)
<223> OTHER INFORMATION: n represents a or g or c or t/u

<400> SEQUENCE: 22
ttgaanccca agctggagct ccccgcggtg gcggccgctc tagaactagt ggatccagat       60
acagttcttg tctttaaact ctgactatgg acaggaatta tatcctgccc acgacccatc      120
cagcctgact gtccacatct tacactctac actcaaggct gaggattcta gattatgaag      180
agttagacat ctaatacatt tctatttaa aaatatagtt gctctgtggt ggggcatggt       240
ggcacatggc tttaatccta gcacccagag gaggtagagg caggtgaatc tctgagttca      300
aggccagcct ggtatatata gcactgactg ctctcccaga ggtcctgagt tcaatttcca      360
gcaaccatat ggtggctcac aaccatctgg aatggaatcc gatgccctct tctggtgtgt      420
ctgaagacag ctacagtgta ctcatacata caataaataa ttcttaaaaa aaaaaacaaa      480
aacaaaaaca aaaactcaaa cacaaacaaa cagtatatat gtaagatatt atagctaacc      540
acttaagttt attattctct gagcattttt gccagaaagg tctgcttcta ataaacaac      600 aaagcaaaaa caccccaaag tccaaacaaa acccccaaac ttttttagcac aggtagattt     660 ctcaggttat gctcaaaacc ttcattcaaa actgaccgac agcgtgatgg agtgtgggct      720
cagcatgaac aagggcctga acgcatctca ggcaaccacg tgatggctga aacccaacc      780 aaccagtcct gcagttaact ccctgaggct ccaggagttt gagcagcatg gagaacatag      840
cctggaggat gtggagacca cctgcttaaa ggttgatgga ctggtgacat tgacagagga      900
cagaacggtc ctaagctgag tgctgggac aacctcaggg agcatgatgg catccccca       960 gggccattgc tcactgctca ctacgagctg gctctcttac cagctgaagc cgtgcttgtt     1020
ggaggcgtgt cttttccagc agggccgtca atttcaggag ccagttttt tt              1072
```

<210> SEQ ID NO 23
<211> LENGTH: 1104
<212> TYPE: DNA
<213> ORGANISM: Mus musculus
<220> FEATURE:
<221> NAME/KEY: misc_feature
<222> LOCATION: (1)..(1104)
<223> OTHER INFORMATION: n represents a or g or c or t/u

<400> SEQUENCE: 23

| | | | | | |
|---|---|---|---|---|---|
| ttggamracy | sggtaccggg | cccccctcg | cggtcgacgg | tatcgataag | cttgatatcg | 60 |
| aattcctgca | gcccggggga | tcctgctttg | ggaaaaagac | gtcaaactct | tcaaggcggg | 120 |
| accaccgctt | gctgtccctc | tggaaagtcc | acttgccgct | tatggcgcaa | ggctcatctt | 180 |
| catccgaatc | ctcactctga | aaacacagaa | tgaagccatt | tatgtactgg | gccaagcagg | 240 |
| gggcagaagg | cagaacacag | gttaagggcc | aggccacagc | ccaaaggata | ttcccagtgt | 300 |
| ccattgctca | gttctcttat | gtaacaaaga | tggatttaaa | gacattatta | ttgggctgga | 360 |
| gggatggctc | agccgttaag | aacactgacc | gcttttccag | aggtcctgag | ttcaaatccc | 420 |
| agcaaccaca | aggtggctca | acaaccatct | gtaatgagat | ctgatgccct | cttccggtgt | 480 |
| gtctgaagac | agccatagtg | tacttatata | taatataaat | aaatccttaa | aaaaagagac | 540 |
| attattatta | ctttatttta | tttagagaat | gtatttgcat | gtatgtgtat | atgtatggat | 600 |
| gtatatgaat | gttcacaccg | tgttcagacg | actaccagtc | agtgtgagtt | ttctccttca | 660 |
| gtcatataga | actgggtcgt | caggcttggc | aacaggccga | ctgtcattta | accagcccag | 720 |
| atgtaaagac | tttaacagaa | gtctgaccaa | gtgttgccag | ctaaacaagt | cattttattg | 780 |
| aaaccctggc | tcgttgggcc | attcactaat | cgctcacaaa | ggggacctct | gagatgggcc | 840 |
| gaaaattcaa | gcatgcaaaa | tattctgaac | tggaatcaga | gtcaacagtc | gtgggactcc | 900 |
| ctctggattg | cctccagttt | aactgcgtgt | tgacagagtg | tgtttatata | ctcgtgtgca | 960 |
| attaaaaaaa | aaaaaaagct | attttcaaac | agcagaatgg | cagctgagga | ctctaggtcc | 1020 |
| aaagagaaaa | gacanggnat | ttcttttaaa | agaactgaag | accatttaan | cgagccatct | 1080 |
| gtggcagaaa | aggnaaaata | gant | | | | 1104 |

<210> SEQ ID NO 24
<211> LENGTH: 725
<212> TYPE: DNA
<213> ORGANISM: Mus musculus
<220> FEATURE:
<221> NAME/KEY: misc_feature
<222> LOCATION: (1)..(725)
<223> OTHER INFORMATION: n represents a or g or c or t/u

<400> SEQUENCE: 24

| | | | | | |
|---|---|---|---|---|---|
| aanncctga | tatcccggaa | agaagagact | ccggggtggg | ggcttccctg | accaggtgca | 60 |
| ataggtaagg | aagggcgttg | cttctcgatg | catccagagg | tggggaatca | agaagggtct | 120 |
| gcttggtggg | attgagtctg | atatttgcag | tcctgcaaat | tcctagggac | tgcatccaac | 180 |
| caggagaccc | caacaatccc | aacgggaaag | gagtattata | aactgggtat | gaacctttgg | 240 |
| tcatcaagga | tgcagacagt | ggaccctgga | agatggtggt | gtttgaacaa | tatagtcagg | 300 |
| ccttatccac | cgtggggtgt | acttagacgt | gcttaaagtg | cttgcatctt | gattctcctg | 360 |
| cagttccaaa | tcttcggttt | cagccaggca | cagatgagaa | ctactcaggg | gagaaactgt | 420 |
| cttctccgtc | attatacccct | gggtaataga | gtgtgaccgt | gaactactag | caggttgtta | 480 |

```
tagcaatctg gcttataaac ttacattaaa tggggagggt gctcccgatg tgcgtagaca      540
ctatccatct tctataagag gcctgagtgt actgagtcca catatctgct atgtctggaa      600
ccaaccttca ggggttacaa agacagtggg ggtgggggggg aggcagggaa aggaagatcg     660
atgctcttgg ttcctgatga tcagaagatt ggtcccagct tactcctttc cgcctgttct      720
ttttg                                                                  725

<210> SEQ ID NO 25
<211> LENGTH: 528
<212> TYPE: DNA
<213> ORGANISM: Mus musculus
<220> FEATURE:
<221> NAME/KEY: misc_feature
<222> LOCATION: (1)..(528)
<223> OTHER INFORMATION: n represents a or g or c or t/u

<400> SEQUENCE: 25
agacgnggtc ccactgactg tgaacgtgca gcgctcagga cagcccctgc cccagagcat       60
ccagcaggcc atgcgctacc tccgtaacca ctgtctggac caggtgagta cagctgcctg      120
tggatcccac tcgtgggagc ggagctttgg gctgcatgtt ttttttttcta gtttcgtggg     180 gaagggtcct gcttccacac ccatccctgc tgttctcctt ccaaaaggtc gggctcttca      240
ggaagtcagg tgtcaaatcc cggatccagg ctctacgcca gatgaatgaa agcgctgaag      300
ataatgtcaa ctatgaaggc cagtctgctt atgatgtggc agacatgtta aagcaatatt      360
ttcgagatct tcctgagccc ctcatgacga acaaactntn cgaaaccttn ctgcagatct      420
accagtgtaa gcgttctttg gtcttcttaa gnaactgatg tcgggttcat gggaccaact      480
gagcacacaa gccttttna tgccatcctt ttgaaanaaa aacttnat                    528

<210> SEQ ID NO 26
<211> LENGTH: 393
<212> TYPE: DNA
<213> ORGANISM: Mus musculus
<220> FEATURE:
<221> NAME/KEY: misc_feature
<222> LOCATION: (1)..(393)
<223> OTHER INFORMATION: n represents a or g or c or t/u

<400> SEQUENCE: 26
aacanaanat tccggatttc ctcagggacc tggaaanaat tcttgcattc agcaatcatg       60
tgggccagcc cttggantcg ccgctaggtt ttcattcagg tctttctggt ctggtttgcc      120
caaactctgt tttctttgca ttaccctttgg anaaaaattc tctcncttca gggtgttgag    180
gtggaanang dacggagcta ggcacacagc caggttggtg ggagtcatct ggttttcttt      240
cacagccgct gtgacatcgc tcaggaaata aaaaantgtc tgcanaacct cccggttctc      300
ntcgggcagg ancataatgg ccgccttgat ggcttggang cgctggtcct tgggcacata      360
ctggtatatc tgcanggaan gttcggaaaa ttt                                   393

<210> SEQ ID NO 27
<211> LENGTH: 601
<212> TYPE: DNA
<213> ORGANISM: Mus musculus
<220> FEATURE:
<221> NAME/KEY: misc_feature
<222> LOCATION: (1)..(601)
<223> OTHER INFORMATION: n represents a or g or c or t/u

<400> SEQUENCE: 27
ccaagctgaa ttccgggcgc cttgtgcttg ctgtggtggg agcccttgaa gcttcaggct       60
```

```
ctccatgcgt ttgagcaggc tccgcgtctt cgacttggtg ttcttctcgt ggtggccttt      120
catgctaaaa ctgaagctgg acagttcctt gggagacggc aggctggaaa aagagtcatc      180
gttgcctaca aagtgtccgg aggagcagac gctgatgacg gaattggttc ggggcgtant      240
ggcatctcca ctgtgggctg cgtgggtggg gacgctgctg ctggtgctgc tgangcttcg      300
gacagangcc acctcctggt gctcgctgag gtctgtcagc atgctttcgt ggcttgtggc      360
gctttgcaaa cgaaanttgt ctggggaccc agggattgga tcctgctttg ggaaaaagac      420
tcaaactctt caaggcggga ccaccgcttg ctgtccctct ggaaagtcca cttgccgctt      480
atggcgcaag gctcatcttc atccgaatcc tcacttcgct tccggtgaag actaatctcc      540
acttcntgaa tgcacacttg tttanaatat ttaacncctg canaaaacct ccatggcgtc      600
t                                                                     601

<210> SEQ ID NO 28
<211> LENGTH: 260
<212> TYPE: DNA
<213> ORGANISM: Mus musculus
<220> FEATURE:
<221> NAME/KEY: misc_feature
<222> LOCATION: (1)..(260)
<223> OTHER INFORMATION: n represents a or g or c or t/u

<400> SEQUENCE: 28
ggcttangga agtgccgggc ttgtgatctt cgggaatgta gaacaccgtg tcctctgggt       60
agctctcacg gtttttatag ttctgctccg tcncnttgtt caaggtggac tgactgaatg      120
ggtccaancc ctctaaatac atgcccaccc gcttgttaca ggtgctgagg ctccgggtcc      180
tggtgaccgg gctgggtgtg ctgaccgcnc tgctggtctc tgattggctg ctgctgctgc      240
tggtctgggt ggaattagac                                                 260

<210> SEQ ID NO 29
<211> LENGTH: 358
<212> TYPE: DNA
<213> ORGANISM: Mus musculus
<220> FEATURE:
<221> NAME/KEY: misc_feature
<222> LOCATION: (1)..(358)
<223> OTHER INFORMATION: n represents a or g or c or t/u

<400> SEQUENCE: 29
ctgattccgg gttgacatta tcttcagcgc tttcattcat ctggcgtaga gcctggatcc       60
gggatttgac acctgacttc ctgaagancc cgacctggtc cagacagtgg ttacggaggt      120
agcgcatggc ctgctggatg ctctggggca ggggctgtcc tgagcgctgc acgttcacag      180
tcagtgggac cccaaacaca ctccggtcct tgtagtctgg aaccttgatc cttttcatga      240
acttgggcac agcccagctg aanccgtgct tgttggangg cgtgtncttt tccagcaggg      300
ccgtcaattt caggagcgag tntttctgca gcaggttcat ctgggccaca gactggca       358

<210> SEQ ID NO 30
<211> LENGTH: 154
<212> TYPE: DNA
<213> ORGANISM: Mus musculus
<220> FEATURE:
<221> NAME/KEY: misc_feature
<222> LOCATION: (1)..(154)
<223> OTHER INFORMATION: n represents a or g or c or t/u

<400> SEQUENCE: 30
```

-continued

```
aattccgggc gatgtcacag cggctgtgaa agaaaaccag atgactccca ccaacctggc      60
tgtgtgccta gctccgtccc tcttccacct caacaccctg aancnataga attcttctcc     120
aagggtaatg canatgaaaa cagagtttgg gcaa                                 154

<210> SEQ ID NO 31
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: n represents a or g or c or t/u

<400> SEQUENCE: 31
aagctggaat ccggtgcgct ccagccttga gccatggctg tgcgtcctcg ctgttggagc      60
cacggctccc cagctccgtg ccccgctccc tgagagtgct cccttcgcgg tggcaatcta    120
aaacccacga ttttgcccga gctggggcga agcgtaagga agctgcgaac cangatgtgc    180
tgacgaccgc gaggggctcg cgtcccggct gccaccgtgg gtcccgacgt gggatcccga    240
tnacttctgg cngcctcgac tttcccagtg cgctcccgtc gncctgcgcc gacc           294
```

DLC-1 GENE DELETED IN CANCERS

CROSS REFERENCE TO RELATED APPLICATIONS

This application is a continuation of prior U.S. application Ser. No. 09/644,947, filed Aug. 23, 2000 now U.S. Pat. No. 6,897,018, which claims priority under 35 U.S.C. §120 from International Application No. PCT/US99/04164, filed Feb. 25, 1999, and under 35 U.S.C. §119 from U.S. Provisional Application No. 60/075,952, filed Feb. 25, 1998. The prior applications are incorporated herein by reference in their entirety.

FIELD OF THE INVENTION

The present invention relates to the cloning and sequencing of the human cDNA molecule corresponding to a newly discovered gene, called DLC-1, which is frequently deleted in liver, breast and colon cancer cells. In addition, lower DLC-1 expression is frequently observed in liver, colon, and prostate cancer cells, compared to normal tissue. The present invention also relates to methods for screening and diagnosis of a genetic predisposition to liver cancer and other cancer types, and methods of gene therapy utilizing recombinant DNA technologies.

BACKGROUND OF THE INVENTION

The isolation of genes involved in human cancer development is critical for uncovering the molecular basis of cancer. One theory of cancer development holds that there are tumor suppressor genes in all normal cells which, when they become non-functional due to mutations, cause neoplastic development (Knudsen et al., *Cancer Res.* 45:1482, 1985). Evidence to support this theory has been found in the cases of human retinoblastoma and colorectal tumors (see U.S. Pat. No. 5,330,892 and references cited therein), as well as in connection with breast and ovarian cancers (see U.S. Pat. Nos. 5,693,473 and references cited therein).

More particularly, recurrent deletions on the short arm of human chromosome 8 in cases of liver, breast, lung and prostate cancers have raised the possibility of the presence of tumor suppressor genes in that location. For example, loss on the short arm of chromosome 8 in prostrate cancer (PC) cells was described in Brothman (*Cancer Genet. Cytogenet.* 95:116-21, 1997). Similar deletions on the short arm of chromosome 8 also have been detected in primary hepatocellular cancer (HCC), non-small cell lung carcinoma (NSCLC) and node-negative breast carcinomas (Isola, *Am. J. Pathol.* 147: 905-11, 1995; and Marchio, et al., *Genes Chromo. Canc.* 18:59-65, 1997).

While recurrent chromosome 8 deletions in malignant tumors support the relevance of this lesion in carcinogenesis, scientists previously have been unable to identify the tumor suppressor genes involved in such deletions. This lack of knowledge concerning the molecular genetic basis of HCC, and other cancers associated with chromosome 8 deletions, has hampered efforts to diagnose the predisposition to such diseases and to develop more effective treatments aimed at curing genetic deficiencies.

Therefore, it is an object of the present invention to provide a human cDNA molecule corresponding to a previously unknown gene located on the short arm of chromosome 8, the deletion of which appears to be closely associated with the development of HCC and other cancers. The cloning and sequencing of such a cDNA molecule enables new and improved methods of diagnosis and treatment of such diseases.

SUMMARY OF THE INVENTION

The present invention discloses the discovery of new human gene involved in the pathogenesis of hepatocellular cancer (HCC), the most common primary liver cancer, and one of the most common cancers in the world, with 251,000 new cases reported each year. (Simonetti et al., *Dig. Dis. Sci.* 36:962-72, 1991; Harris et al., *Cancer Cells* 2:146-8, 1990; Marchio, et al., *Genes Chromo. Cancer* 18:59-65, 1997). More specifically, the present invention discloses the isolation of the full length cDNA and the chromosomal localization of a new gene which is frequently deleted in liver cancer, and hence is named the DLC-1 gene.

The full-length cDNA for DLC-1 is 3850 bp long (Seq. I.D. No. 1), encodes a protein of 1091 amino acids (Seq. I.D. No. 2), and was localized by fluorescence in situ hybridization to chromosome 8 at bands p21.3-22. Because the DLC-1 gene is deleted from a significant percentage of primary HCC tumor cells and cell lines, primary breast cancers (BC), and colorectal cancer (CRC) cell lines, and its expression is decreased or not observed in a significant percentage of HCC cell lines, CRC cell lines and prostate cancer (PC) cell lines, the DLC-1 gene appears to operate as a tumor suppressor in liver cancer and other cancers including PC, CRC and BC.

The object of identifying the hitherto unknown DLC-1 gene has been achieved by providing an isolated human cDNA molecule which is able specifically to correct the cellular defects characteristic of cells from patients with a deleted or mutated DLC-1 gene. Specifically, the invention provides, for the first time, an isolated cDNA molecule which, when transfected into cells derived from a patient with a deleted or mutated DLC-1 gene, can produce the DLC-1 protein believed to be active in suppressing HCC pathogenesis and other cancers, such as breast, colorectal, and prostate cancers. The invention encompasses the DLC-1 cDNA molecule (derived from normal human liver cells), the nucleotide sequence of this cDNA, and the putative amino acid sequence of the DLC-1 protein encoded by this cDNA.

Having herein provided the nucleotide sequence of the DLC-1 cDNA, correspondingly provided are the complementary DNA strands of the cDNA molecule and DNA molecules which hybridize under stringent conditions to the DLC-1 cDNA molecule or its complementary strand. Such hybridizing molecules include DNA molecules differing only by minor sequence changes, including nucleotide substitutions, deletions and additions. Also comprehended by this invention are isolated oligonucleotides comprising at least a segment of the cDNA molecule or its complementary strand, such as oligonucleotides which may be employed as effective DNA hybridization probes or primers useful in the polymerase chain reaction or as hybridization probes. Such probes and primers are particularly useful in the screening and diagnosis of persons genetically predisposed to HCC, and other cancers, as the result of DLC-1 gene deletions.

Hybridizing DNA molecules and variants on the DLC-1 cDNA may readily be created by standard molecular biology techniques. Through the manipulation of the nucleotide sequence of the human cDNA provided by this invention by standard molecular biology techniques, variants of the DLC-1 protein may be made which differ in precise amino acid sequence from the disclosed protein yet which maintain the essential characteristics of the DLC-1 protein or which are selected to differ in one or more characteristics from this protein. Such variants are another aspect of the present invention.

Also provided by the present invention are recombinant DNA vectors comprising the disclosed DNA molecules, and transgenic host cells containing such recombinant vectors.

Having isolated the human DLC-1 cDNA sequence, the genomic sequence for the gene was determined according to the following method: A human genomic library constructed using the P1 vector, pAD10SacBII, was transferred from its original *E. coli* host into a second *E. coli* host, strain N3516, following procedures well-known in the art. A positive P1 clone containing the DLC-1 gene was then obtained by performing a protocol of PCR-based P1 library screening (Sheperd, *Proc. Natl. Acad. Sci. USA* 91:2629-33, 1994; Neuhausen, *Hum. Mol. Genet.* 3:1919-26, 1994). The PCR primers used in this screening, designed from a genomic fragment isolated through Representational Difference Analysis (described more fully below), are listed below:

PL7-3F 5' GACACCACCATCTCTGTGCTC 3' (Seq. I.D. No. 7)

PL7-3R 5' GCAGACTGTCCTTCGTAGTTG 3' (Seq. I.D. No. 8)

An isolated and purified biological sample of this genomic DLC-1 gene was deposited with the American Type Culture Collection (ATCC) in Manassas, Va., on Feb. 25, 1998, under accession number 98676. The present invention also provides for the use of the DLC-1 cDNA, the corresponding genomic gene and of the DLC-1 protein, and derivatives thereof, in aspects of diagnosis and treatment of HCC, and other cancers including, but not limited to PC, BC and CRC, resulting from DLC-1 deletion or mutation.

An embodiment of the present invention is a method for screening a subject to determine if the subject carries a mutant DLC-1 gene, or if the gene has been partially or completely deleted, as is thought to occur in many HCC cases. The method comprises the steps of: providing a biological sample obtained from the subject, which sample includes DNA or RNA, and providing an assay for detecting in the biological sample the presence of a mutant DLC-1 gene, a mutant DLC-1 RNA, or the absence, through deletion, of the DLC-1 gene and corresponding RNA.

The foregoing assay may be assembled in the form of a diagnostic kit and preferably comprises either: hybridization with oligonucleotides; PCR amplification of the DLC-1 gene or a part thereof using oligonucleotide primers; RT-PCR amplification of the DLC-1 RNA or a part thereof using oligonucleotide primers; or direct sequencing of the DLC-1 gene of the subject's genome using oligonucleotide primers. The efficiency of these molecular genetic methods should permit a rapid classification of patients affected by deletions or mutations of the DLC-1 gene.

A further aspect of the present invention is a method for screening a subject to assay for the presence of a mutant or deleted DLC-1 gene, comprising the steps of: providing a biological sample of the subject which sample contains cellular proteins, and providing an immunoassay for quantitating the level of DLC-1 protein in the biological sample. Diagnostic methods for the detection of mutant or deleted DLC-1 genes made possible by this invention will provide an enhanced ability to diagnose susceptibility to HCC and other cancers such as PC, BC and CRC.

Another aspect of the present invention is an antibody preparation comprising antibodies that specifically detect the DLC-1 protein, wherein the antibodies are selected from the group consisting of monoclonal antibodies and polyclonal antibodies.

Those skilled in the art will appreciate the utility of this invention is not limited to the specific experimental modes and materials described herein.

The foregoing and other features and advantages of the invention will become more apparent from the following detailed description and accompanying drawings.

BRIEF DESCRIPTION OF DRAWINGS

FIG. 3 is a digital image of a Southern blot which compares representative primary human breast cancers (T) with healthy normal blood cells (N) from the same patient, and demonstrates a genomic deletion of the DLC-1 gene in 7 of 15 primary breast cancers. A representative 10 of the 15 primary tumors are shown. DNA was digested with either (a) BglII or (b) BamHI. Cell lines IC11T, IC12T, IC13T, IC2T, IC6T, and IC7T showed reduction of DNA intensity compared with normal DNA.

FIG. 4 is a digital image of a Southern blot which compares representative human colon cancer cell lines with normal DNA (lane 1), and demonstrates a genomic deletion of the DLC-1 gene in two out of five colon cancer cell lines. Cell lines SW1116 and SW403 (lanes 5 and 6) showed reduction of DNA intensity compared with normal DNA (lane 1).

FIG. 5 is a digital image of a Northern blot showing the mRNA expression of the DLC-1 gene in normal human tissues. The DLC-1 gene is expressed in all normal tissues tested as a 7.5 kb major transcript and a 4.5 kb minor transcript.

FIG. 6 is a digital image of a Northern blot comparing the mRNA expression of DLC-1 gene in normal human tissues (NL-RNA) and HCC cell lines. DLC-1 mRNA expression was decreased or not detected in the WRL, 7703, Chang and Focus HCC cell lines.

SEQUENCE LISTING

Figures 1, 2:
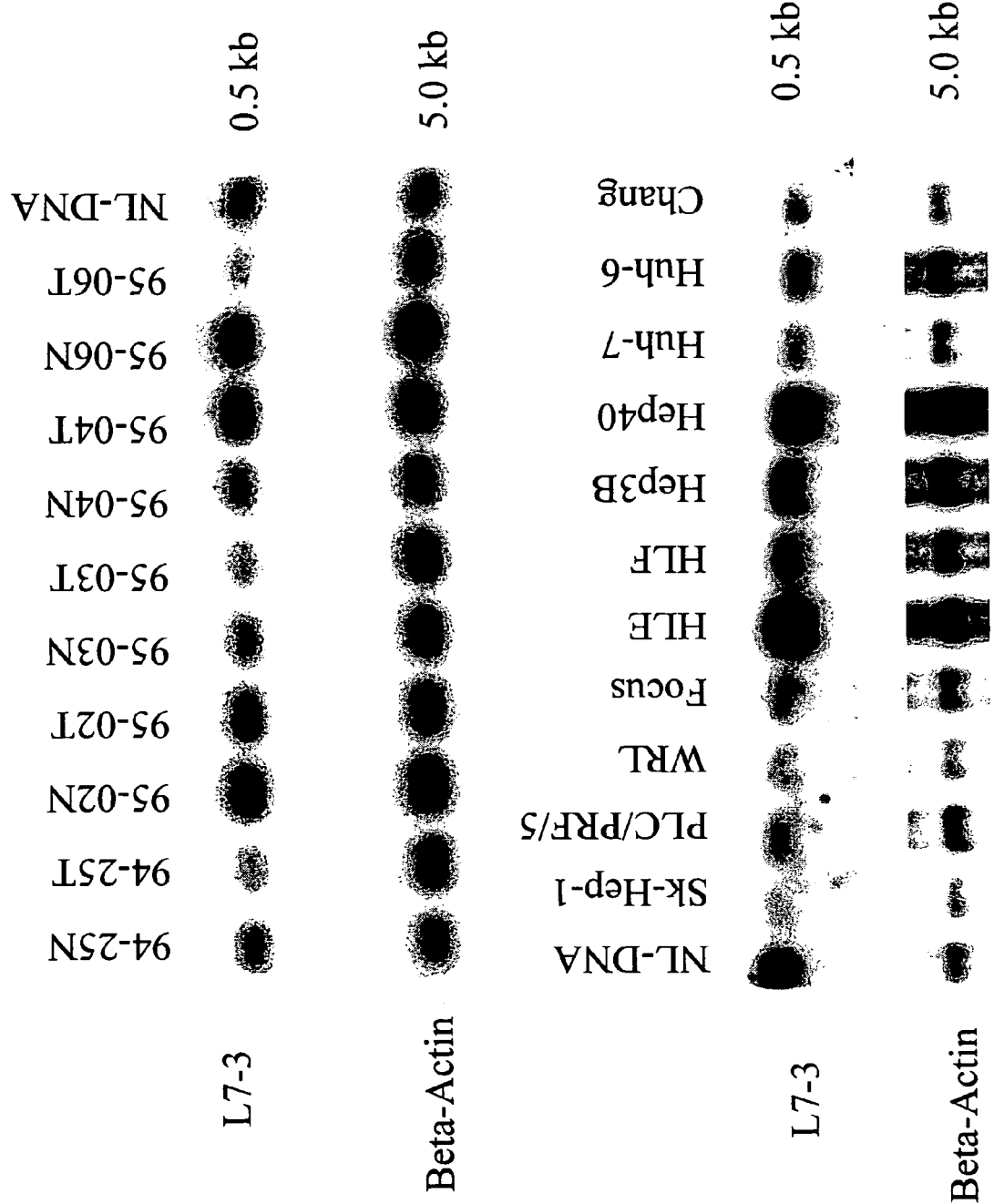
FIG. 1 is a digital image of a Southern blot which compares primary HCC tumor cells (T) with healthy normal liver cells (N), and demonstrates a genomic deletion of the L7-3 clone in the HCC cells. Primary tumors 94-25T, 95-03T and 95-06T showed 50% decrease of DNA intensity as compared with normal liver tissues.
FIG. 2 is a digital image of a Southern blot which compares representative HCC cell lines with healthy liver cells (NL-DNA), and demonstrates a genomic deletion of the L7-3 clone in 9 of 11 HCC cell lines. Cell lines Sk-Hep-1, PLC/PRF/5, WRL, Focus, HLF, Hep3B, Huh-7, Huh-6, Chang showed reduction of DNA intensity compared with human normal liver genomic DNA.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

Seq. I.D. No. 1 is the nucleotide sequence of the human DLC-1 cDNA.

Seq. I.D. No. 2 is the amino acid sequence of the human DLC-1 protein.

Seq. I.D. Nos. 3-4 are oligonucleotide sequences of PCR primers which can be used to amplify the entire DLC-1 cDNA molecule.

Seq. I.D. Nos. 5-6 are oligonucleotide sequences of PCR primers which can be used to amplify the open reading frame of the DLC-1 cDNA molecule.

Seq. I.D. Nos. 7-8 are the oligonucleotide sequences of PCR primers used to screen a human genomic library.

Seq. I.D. Nos. 9-11 are the oligonucleotide sequences of the primers used for 5' and 3' RACE.

Seq. I.D. No. 12 is the nucleotide sequence for the L7-3 probe.

Seq. I.D. No. 13 is the nucleotide sequence for the P-35 probe.

Seq. I.D. No. 14 is the nucleotide sequence for part of the human genomic DLC-1 sequence.

Seq. I.D. No. 15 is the nucleotide sequence for part of the human genomic DLC-1 sequence.

Seq. I.D. No. 16 is the nucleotide sequence for part of the human genomic DLC-1 sequence.

Seq. I.D. No. 17 is the nucleotide sequence for part of the human genomic DLC-1 sequence.

Seq. I.D. No. 18 is the nucleotide sequence for part of the human genomic DLC-1 sequence.

Seq. I.D. No. 19 is the nucleotide sequence for part of the human genomic DLC-1 sequence.

Seq. I.D. No. 20 is the nucleotide sequence for part of the mouse genomic DLC-1 sequence.

Seq. I.D. No. 21 is the nucleotide sequence for part of the mouse genomic DLC-1 sequence.

Seq. I.D. No. 22 is the nucleotide sequence for part of the mouse genomic DLC-1 sequence.

Seq. I.D. No. 23 is the nucleotide sequence for part of the mouse genomic DLC-1 sequence.

Seq. I.D. No. 24 is the nucleotide sequence for part of the mouse genomic DLC-1 sequence.

Seq. I.D. No. 25 is the nucleotide sequence for part of the mouse genomic DLC-1 sequence.

Seq. I.D. No. 26 is the nucleotide sequence for a cDNA fragment of the mouse DLC-1 sequence.

Seq. I.D. No. 27 is the nucleotide sequence for a cDNA fragment of the mouse DLC-1 sequence.

Seq. I.D. No. 28 is the nucleotide sequence for a cDNA fragment of the mouse DLC-1 sequence.

Seq. I.D. No. 29 is the nucleotide sequence for a cDNA fragment of the mouse DLC-1 sequence.

Seq. I.D. No. 30 is the nucleotide sequence for a cDNA fragment of the mouse DLC-1 sequence.

Seq. I.D. No. 31 is the nucleotide sequence for a cDNA fragment of the mouse DLC-1 sequence.

DETAILED DESCRIPTION OF THE INVENTION

The present invention discloses the isolation of the full length cDNA and the chromosomal localization of a new gene, called the DLC-1 gene. As discussed in Examples 1-3 below, deletion of the DLC-1 gene has been detected in about half of the primary HCC tumor cells and in a majority of the HCC cell lines which were studied. In addition, studies of other cancers revealed that DLC-1 was also deleted in 7 of 15 primary breast cancers and in 2 of 5 CRC cell lines. Moreover, the DLC-1 gene was not expressed in 29% of HCC cell lines, 64% of CRC cell lines and 67% of PC cell lines. These frequent deletions suggest that the DLC-1 gene is a tumor suppressor gene for HCC as well as PC, BC and CRC.

The full-length cDNA for DLC-1 is 3850 bp long (Seq. I.D. No. 1) and encodes a protein of 1091 amino acids (Seq. I.D. No. 2). Fluorescent in situ hybridization has generally localized the gene on the short arm of chromosome 8 at bands p21.3-22.

Further evidence that the DLC-1 gene acts as a tumor suppressor is found in its 86% homology with the rat p122 RhoGAP gene (Homma and Emori, *EMBO. J.* 14:286-91, 1995). The rat p122 RhoGAP gene encodes a GTPase activating protein that catalyzes the conversion of the active GTP-bound Rho complex to an inactive GDP-bound one. The Rho family proteins, a subfamily of the Ras small GTP binding superfamily, function as important regulators in the organization of actin cytoskeleton (Nobes, et al., *Cell* 81:53-62, 1995). Rho proteins are also involved in Ras-mediated oncogenic transformation (Khosravi-Far, et al., *Adv. Cancer Res.* 69:59-105, 1997). GAP genes may function as tumor suppressors by down-regulating oncogenic Rho proteins (Quilliam, et al. *Bioessays* 17:395-404, 1995; Wang, et al., *Cancer Res.* 57:2478-84, 1997). Based on its substantial homology with the rat p122 RhoGAP gene, it appears likely the DLC-1 gene is a human RhoGAP gene involved in the suppression of HCC tumors.

Definitions

In order to facilitate review of the various embodiments of the invention, the following definition of terms is provided:

Breast Carcinoma (BC): breast cancer thought to result, in some instances, from the deletion or mutation of the DLC-1 tumor suppressor gene.

cDNA (complementary DNA): a piece of DNA lacking internal, non-coding segments (introns) and regulatory sequences which determine transcription. cDNA is synthesized in the laboratory by reverse transcription from messenger RNA extracted from cells.

Colorectal Carcinoma (CRC): colorectal cancer (such as adenocarcinoma) thought to result, in some instances, from the deletion or mutation of the DLC-1 tumor suppressor gene.

Deletion: the removal of a sequence of DNA, the regions on either side being joined together.

DLC-1 gene: a gene, the mutation of which is associated with hepatocellular, breast, colon and prostate carcinomas, and particularly adenocarcinomas of those organs A mutation of the DLC-1 gene may include nucleotide sequence changes, additions or deletions, including deletion of large portions or all of the DLC-1 gene. The term "DLC-1 gene" is understood to include the various sequence polymorphisms and allelic variations that exist within the population. This term relates primarily to an isolated coding sequence, but can also include some or all of the flanking regulatory elements and/or intron sequences.

DLC-1 cDNA: a mammalian cDNA molecule which, when transfected into DLC-1 cells, expresses the DLC-1 protein. The DLC-1 cDNA can be derived by reverse transcription from the mRNA encoded by the DLC-1 gene and lacks internal non-coding segments and transcription regulatory sequences present in the DLC-1 gene.

DLC-1 protein: the protein encoded by the DLC-1 cDNA, the altered expression or mutation of which can predispose to the development of certain cancers, such as hepatocellular carcinoma. This definition is understood to include the various sequence polymorphisms that exist, wherein amino acid substitutions in the protein sequence do not affect the essential functions of the protein.

DNA: deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Hepatocellular carcinoma (HCC): liver cancer thought to result, in some instances, from the deletion or mutation of the DLC-1 tumor suppressor gene.

Isolated: requires that the material be removed from its original environment. For example, a naturally occurring DNA molecule present in a living animal is not isolated, but the same DNA molecule, separated from some or all of the coexisting materials in the natural system, is isolated.

Mutant DLC-1 gene: a mutant form of the DLC-1 gene which in some embodiments is associated with hepatocellular, breast, colon and/or prostate carcinoma.

Mutant DLC-1 RNA: the RNA transcribed from a mutant DLC-1 gene.

Mutant DLC-1 protein: the protein encoded by a mutant DLC-1 gene.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (*Molecular Cloning: A Laboratory Manual*, Cold Spring Harbor, N.Y., 1989) and Ausubel et al. (*Current Protocols in Molecular Biology*, Greene Publishing Associates and Wiley-Intersciences, 1987).

Primers are short nucleic acids, for example DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (*Molecular Cloning: A Laboratory Manual*, Cold Spring Harbor, N.Y., 1989), Ausubel et al. (*Current Protocols in Molecular Biology*, Greene Publishing Associates and Wiley-Intersciences, 1987), and Innis et al., (*PCR Protocols, A Guide to Methods and Applications*, Innis et al. (eds.), Academic Press, Inc., San Diego, Calif., 1990). PCR primer pairs can be derived from a known sequence, for example, by using computer programs intended for that purpose such as Primer (Version 0.5, ©1991, Whitehead Institute for Biomedical Research, Cambridge, Mass.).

Prostate Carcinoma (PC): prostate cancer (such as prostatic adenocarcinoma) thought to result, in some instances, from the deletion or mutation of the DLC-1 tumor suppressor gene.

Protein: a biological molecule expressed by a gene and comprised of amino acids.

Purified: the term "purified" does not require absolute purity; rather, it is intended as a relative term. Thus, for example, a purified protein preparation is one in which the protein referred to is more pure than the protein in its natural environment within a cell.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Representational Difference Analysis (RDA): a PCR-based subtractive hybridization technique used to identify differences in the mRNA transcripts present in closely related cell lines.

Sequence identity: the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, Methods in *Mol. Biol.* 24:307-31, 1988; Higgins and Sharp, *Gene* 73:237-44, 1988; Higgins and Sharp, *CABIOS* 5:151-3, 1989; Corpet et al., *Nuc. Acids Res.* 16:10881-90, 1988; Huang et al., *Comp. Appl. BioSci.* 8:155-65, 1992; and Pearson et al., *Meth. Mol. Biol.* 24:307-31, 1994.

The NCBI Basic Local Alignment Search Tool (BLAST) (Altschul et al., *J. Mol. Biol.* 215:403-10, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at http://www.ncbi.nim.nih.gov/BLAST/. A description of how to determine sequence identity using this program is available at http://www.ncbi.nim.nih.gov/BLAST/blast_help.html.

Homologs of the DLC-1 protein are typically characterized by possession of at least 70% sequence identity counted over the full length alignment with the disclosed amino acid sequence using the NCBI Blast 2.0, gapped blastp set to default parameters. Such homologous peptides will more preferably possess at least 75%, more preferably at least 80% and still more preferably at least 90% or 95% sequence identity determined by this method. When less than the entire sequence is being compared for sequence identity, homologs will possess at least 75% and more preferably at least 85% and more preferably still at least 90% or 95% sequence identity over short windows of 10-20 amino acids. Methods for determining sequence identity over such short windows are described at http://www.ncbi.nlm.nih.gov/BLAST/blast_FAQs.html. One of skill in the art will appreciate that these sequence identity ranges are provided for guidance only; it is entirely possible that strongly significant homologs or other variants could be obtained that fall outside of the ranges provided.

The present invention provides not only the peptide homologs that are described above, but also nucleic acid molecules that encode such homologs.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

VNTR probes: Variable Number of Tandem Repeat probes. These are highly polymorphic DNA markers for human chromosomes. The polymorphism is due to variation in the number of tandem repeats of a short DNA sequence. Use of these probes enables the DNA of an individual to be distinguished from that derived from another individual.

Tumor: a neoplasm

Neoplasm: abnormal growth of cells

Cancer: malignant neoplasm that has undergone characteristic anaplasia with loss of differentiation, increased rate of growth, invasion of surrounding tissue, and is capable of metastasis.

Malignant: cells which have the properties of anaplasia invasion and metastasis.

Normal cells: Non-tumor, non-malignant cells

Mammal: This term includes both human and non-human mammals. Similarly, the term "patient" includes both human and veterinary subjects.

Animal: Living multicellular vertebrate organisms, a category which includes, for example, mammals and birds.

Transgenic Cell: transformed cells which contain foreign, non-native DNA.

Additional definitions of common terms in molecular biology may be found in Lewin, B. "Genes V" published by Oxford University Press.

Materials and Methods

Primary HCC Samples and HCC Cell Lines

All of the primary liver tumor DNAs were obtained from surgical resection of HCC tissues from patients in Qidong, China. Each tumor sample was matched with its surrounding non-cancerous liver tissue. DNAs were extracted after diagnosis of HCC with or without cirrhosis. The tumors were Hepatitis B virus (HBV) positive for HBVsAg and/or PCR detection of HBVx gene. HCC cell lines were obtained from ATCC (Manassas, Va.), Qidong Liver Cancer Institute, China, and Dr. Curtis C. Harris (Laboratory of Human Carcinogenesis, Division of Basic Sciences, National Cancer Institute) (Wang, et al., *Chin. J. Oncol.* 3:241-4, 1981).

Breast, Prostate and Colorectal Carcinomas

All normal and CRC (adenocarcinomas) cell lines were purchased from ATCC (Manassas, Va.). The PC cell lines (also adenocarcinomas) were obtained from The University of Texas M.D. Anderson Cancer Center (Houston, Tex.). The DNA from primary breast carcinomas and blood cells were obtained from patients in Iceland.

Manipulation of Genetic Material

Unless otherwise specified, manipulation of genetic material was performed according to standard laboratory procedures, such as those described in Sambrook et al. (*Molecular Cloning: A Laboratory Manual*, Cold Spring Harbor, N.Y., 1989) and Ausubel et al. (*Current Protocols in Molecular Biology*, Greene Publishing Associates and Wiley-Intersciences, 1987).

Representational Difference Analysis (RDA)

One primary HCC, having a homozygous point mutation of the p53 gene, but not in its surrounding, non-cancerous liver tissue, was selected for analysis. RDA was performed as originally described in Lisitsyn et al. (*Proc. Natl. Acad. Sci. USA* 92:151-5, 1995), with tumor DNA as tester and normal liver DNA as driver. BglII (Promega, Madison, Wis.) was chosen as the restriction enzyme and its adaptors were used for direct preparation of amplicons and PCR-based subtractive hybridization. The final difference products showing distinct bands in agarose gel were recovered after BglII digestion and ligated into the BglII site of dephosphorylated pSP72 vector (Promega). The recombinant difference products were then transfected into *E. coli* DH10B.

Characterization of RDA Probes

Plasmids with distinct DNA inserts were selected for further analysis. DNA sequencing was performed using the Dye Terminator Cycle DNA Sequencing kit (Perkin Elmer, Rockville, Md.). Sequencing reaction products were purified by spin columns (Princeton Separations, Adelphia, N.J.), and run on a 377 DNA Sequencer (Perkin Elmer/Applied Biosystems, Foster City, Calif.). The homology analysis was carried out by BLAST search of the GenBank DNA databases (Altschul, et al., *J. Mol. Biol.* 215:403-10, 1990). The RDA products that elicited significant homology or appeared in multiple clones, were selected for further Southern blot and/or Northern blot analysis.

Conditions for Southern Analysis

Genomic DNA was isolated from tumor and non-tumor cell lysates and digested with restriction enzymes. The digested DNA was separated by electrophoresis in a 1% agarose gel and transferred to nylon membrane for hybridization. 50 ng of DNA probe was radio-labeled (Prime-It RmT, Stratagene) as per the manufacturers instructions and used for hybridization. A probe for beta-actin was used as a standard to control for the amount of DNA loaded. Hybridization was performed at 68° C. for 2-4 hours using Quickhybrid solution (Stratagene). Following hybridization, the membranes were washed three times at 37° C. for 10 min in 1×SSC solution containing 0.1×SDS. This was followed by a single wash at 62° C. for 30 min in 0.1×SSC solution containing 0.1×SDS. Blots were exposed to a Phospholmager, and analyzed using Software ImageQuant Version 3.3 (Molecular Dynamics, Sunnyvale, Calif.) for quantitative analysis.

Conditions for Northern Analysis

Total RNA was extracted from cell lysates using TRIzol solution (Gibco-BRL), which was then separated in a 1% agarose gel and transferred to nylon membrane for hybridization. 50 ng of DNA probe was radio-labeled (Prime-It RmT, Stratagene) as per the manufacturers instructions and used for hybridization. A probe for GAPDH or beta-actin was used as a control for the amount of RNA loaded. Hybridization, washing, and analysis was performed as described above for Southern Hybridization.

5' and 3' RACE and cDNA Library Screening for cDNA Cloning

5' and 3' RACE (Rapid Amplification of cDNA Ends) were started from a deleted fragment detected with RDA, and performed using human placenta Marathon™ cDNA as template (Clontech, Inc., Palo Alto, Calif.). The primers used for RACE, generated from the L7-3 sequence (Seq. I.D. No. 12), are as follows:

PrRACE5: 5'CACTCCGGTCCTTGTAGTCTGGAACC 3' (Seq. I.D. No. 9) was used for the first round of PCR for 5' RACE.

PrPACE5N: 5' ATCCTCTTCATGAACTCGGGCACGG 3' (Seq. I.D. No. 10) was used as the nested primer in the second round of 5' RACE.

PrRACE3: 5' GATCAAGGTTCTAGACTACAAG-GACCG 3' (Seq. I.D. No. 11) was used for 3' RACE.

The final 5' RACE product, exhibiting the same band pattern as the deleted fragment in Northern blot hybridization, was labeled with α-[$^{32}$P]-dCTP to screen a 5' Strech cDNA library constructed from human lung tissue (Clontech, Inc.). The lambda DNA of positive clones was converted into plasmid DNA by transfecting lambda DNA into AM1 bacterial cells. The full-length cDNA sequencing of positive clones was completed by primer walking and assembled by Sequencher™ 3.1 program.

Fluorescence in situ Hybridization (FISH) Gene Mapping and Comparative Genomic Hybridization (CGH)

A genomic probe isolated from human P1 library was labeled with biotin and used for FISH chromosomal localization and CGH analysis. For both analyses, chromosomes prepared from methotrexate-synchronized normal peripheral lymphocyte cultures were used. The original CGH protocol, described in Kallioniemi et al. (*Science* 258:818-21, 1992), was employed with minor modifications. The conditions of hybridization, the detection of hybridization signals, digital-image acquisition, processing and analysis, and direct fluorescent signal localization on banded chromosomes were performed as previously described in Zimonjic et al. (*Cancer Genet Cytogenet.* 80:100-2, 1995).

The following examples are illustrative of the scope of the present invention.

EXAMPLE 1

Detection of DLC-1 Deletion in Liver Cancer Cells by RDA

Primary HCC tumor samples, matched with surrounding non-cancerous liver tissue, were obtained as described above and analyzed by RDA. Several RDA difference products were observed after the third round of hybridization/selection as distinct bands in agarose gel. Twenty individual fragments were isolated and analyzed by Southern blot hybridization for deletions. One clone, L7-3, of 600 bp (Seq. I.D. No. 12), showed loss of heterozygosity (LOH) in the primary tumor (FIG. 1). BLAST search revealed that the L7-3 clone had homology to rat p122 RhoGAP cDNA (Homma and Emori, *EMBO. J.* 14:286-91, 1995).

EXAMPLE 2

Southern Analysis

HCC Cell Lines

To determine if the L7-3 clone is represented in a region recurrently deleted in HCC, 15 primary HCC tumors and 11 HCC-derived cell lines were examined using Southern analysis as described above. The DNA was digested with BglII, and probed with L7-3 (Seq. I.D. No. 12). Seven of the fifteen primary HCC tumors (representatives are shown in FIG. 1) and 9 of the 11 HCC cell lines (FIG. 2) had a genomic deletion of the L7-3 clone compared to no deletions in the normal liver cells.

Primary Breast Carcinomas

Using Southern analysis as described above, primary human breast cancer and corresponding patient blood cell DNA was digested with BglII (FIG. 3*a*) or BamHI (FIG. 3*b*) and probed with full-length DLC-1 cDNA (Seq. I.D. No. 1). Genomic deletions of DLC-1 gene were detected in 7 of 15 human primary breast cancers (representatives are shown in FIG. 3). Deletions were noted if the DNA intensity of the tumor tissues exhibited at least half the intensity when compared with their normal tissue DNA. Samples IC11T, IC12T, IC13T, IC2T, IC6T, IC7T are representative for the genomic deletions in these experiments.

Southern analysis of these cells resulted in several bands. As a control for DNA loading, the bands that remained unchanged in the tumor cells were used.

Colon Carcinoma Cell Lines

Using Southern analysis as described above, normal genomic DNA (Promega) and the DNA from five CRC cell lines were digested with EcoRI, and probed with a mixture of L7-3 and P-35 (Seq. I.D. Nos. 12 and 13) which correspond to exon 2 and exon 7 of the human DLC-1 gene (see FIG. 9), respectively. Genomic deletions of DLC-1 gene were detected in two of five human CRC cell lines (FIG. 4). Cell lines SW403 and SW1116 showed half of the DNA intensity for probe P-35 when compared with normal genomic DNA (compare lanes 5 and 6 with lane 1). Interestingly, the signal was unaltered when the L7-3 probe was used, indicating that this region (exon 2) is not responsible for the development of CRC in these cell lines. Therefore, the signal from L7-3 can be used as an internal control for the amount of DNA loaded.

EXAMPLE 3

Northern Analysis

HCC Cell Lines

Considering the significant DNA sequence homology of the L7-3 clone with rat RhoGAP cDNA, its mRNA expression was examined in both normal human tissues and HCC-derived cell lines by Northern analysis as described above. Analysis of mRNA isolated from several normal human tissues, including liver, demonstrated that the L7-3 clone (Seq. I.D. No. 12) hybridized to a 7.5 kb (major) transcript and a 4.5 kb (minor) transcript (FIG. 5) that were detected in all normal tissues but not in 4 (WRL, 7703, Chang and Focus) out of 14 human HCC-derived cell lines (FIG. 6).

Colorectal Carcinomas

Figure 7:
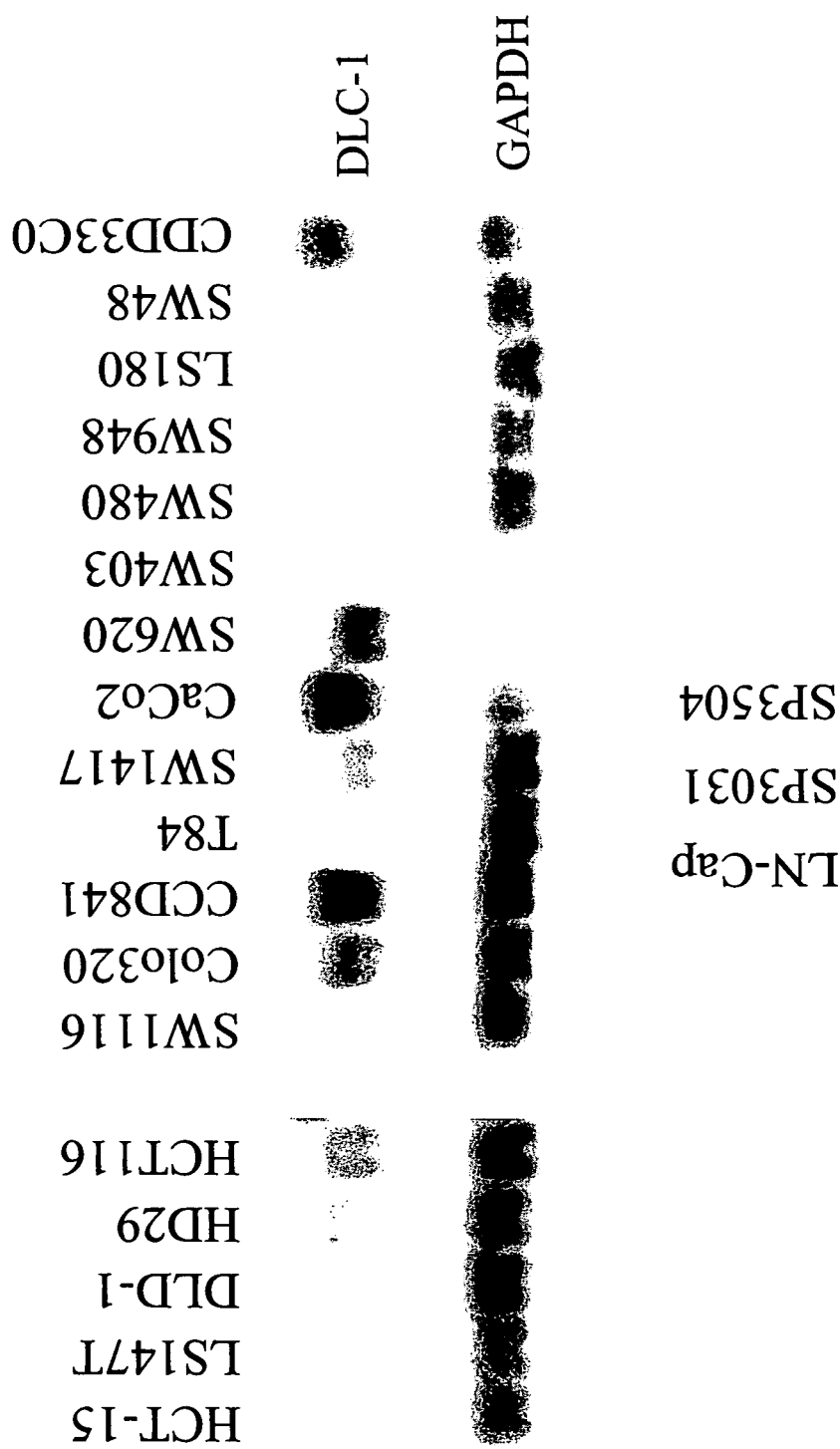
FIG. 7 is a digital image of a Northern blot comparing the mRNA expression of DLC-1 gene in normal human tissues (CDD33C0) and human colon cancer cell lines. DLC-1 mRNA was expression was decreased or not detected in HCT-15, LS147T, DLD-1, HD29, SW1116, T84, SW1417, SW403, SW948, LS180, and SW48 cell lines.

Using Northern analysis as described above, RNA from normal and CRC cell lines was prepared and probed with the full-length DLC-1 cDNA (Seq. I.D. No. 1). In human CRC cell lines, 11 out of 17 (HCT-15, LS147T, DLD-1, HD29, SW1116, T84, SW1417, SW403, SW948, LS180, SW48) showed noticeably decreased or no expression of DLC-1 mRNA (FIG. 7). In this experiment, the normal human colon fibroblast cell line CDD33C0 was used as a normal control.

Prostate Carcinomas

Figure 8:
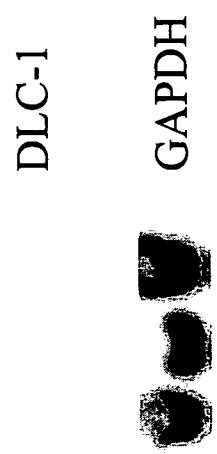
FIG. 8 is a digital image of a Northern blot showing the mRNA expression of DLC-1 gene in three human prostate cancer cell lines. DLC-1 mRNA was not detected in the LN-Cap and SP3504 cell lines.

Using Northern analysis as described above, RNA from PC cell lines was prepared and probed with the full-length DLC-1 cDNA (Seq. I.D. No. 1). Low levels or no DLC-1 gene expression was demonstrated by in two (LN-Cap and SP3504) out of three human PC cell lines (FIG. 8).

EXAMPLE 4

Obtaining the DLC-1 cDNA

The cDNA for the clone L7-3 was obtained by 5' RACE and 3' RACE coupled with cDNA library screening as described above. The full-length cDNA of DLC-1 gene is 3850 bp long (Seq. I.D. No. 1) and encodes a protein of 1091 amino acids (Seq. I.D. No. 2). The estimated molecular weight of DLC-1 protein is 125 kD. The untranslated regions of 5' end and 3' end of DLC-1 gene are 324 bp and 250 bp, respectively (Seq. I.D. No. 1).

EXAMPLE 5

Chromosomal Localization of Human DLC-1

The DLC-1 gene was chromosomally localized using the materials and methods described above. The majority of metaphases hybridized with biotin or digoxigenin-labeled genomic probe had fluorescent signal at identical sites on both chromatids of the short arm of chromosome 8. The signal was analyzed in 100 metaphases with both homologous labeled. Fifty metaphases were examined by imaging of DAPI generated and enhanced G-like banding. The fluorescent signals were distributed within region 8p21-22 However, over 50% of doublets were at bands 8p21.3-22, the most likely location of the DLC-1 gene.

To further characterize the region harboring the DLC-1 gene, the primary tumor DNA used as tester in RDA (94-25T) was analyzed by CGH. The fluorescence profile for chromosome 8 demonstrated DNA loss on region of 8p23-q11.2 and gain on region of 8q21.1-q24.3.

EXAMPLE 6

Cloning and Characterization of Human DLC-1

The DLC-1 cDNA sequence (Seq. I.D. No. 1) described above does not contain the introns, upstream transcriptional promoter or regulatory regions or downstream transcriptional regulatory regions of the DLC-1 gene. It is possible that some mutations in the DLC-1 gene that may lead to HCC are not included in the cDNA but rather are located in other regions of the DLC-1 gene. Mutations located outside of the open reading frame that encodes the DLC-1 protein are not likely to affect the functional activity of the protein but rather are likely to result in altered levels of the protein in the cell. For example, mutations in the promoter region of the DLC-1 gene may prevent transcription of the gene and therefore lead to the complete absence of the DLC-1 protein in the cell.

Additionally, mutations within intron sequences in the genomic gene may also prevent expression of the DLC-1 protein. Following transcription of a gene containing introns, the intron sequences are removed from the RNA molecule in a process termed splicing prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and may fail to remove the intron. If this occurs, the encoded protein will likely be defective. Thus, mutations inside the intron sequences within the DLC-1 gene (termed "splice site mutations") may also lead to the development of HCC. However, knowledge of the exon structure and intronic splice site sequences of the DLC-1 gene is required to define the molecular basis of these abnormalities. The provision herein of the DLC-1 cDNA sequence (Seq. I.D. No. 1) enables the cloning of the entire DLC-1 gene (including the promoter and other regulatory regions and the intron sequences) and the determination of its nucleotide sequence. With this information in hand, diagnosis of a genetic predisposition to HCC and other cancers based on DNA analysis will comprehend all possible mutagenic events at the DLC-1 locus.

The ATCC deposit (98676) of the genomic DLC-1 gene may be utilized in aspects of the present invention. Alternatively, the DLC-1 gene may be isolated by one or more routine procedures, including PCR-based screening of a human genomic P1 library as described above. Alternatively, the method described in WO 93/22435 can be utilized. For example, a YAC library of human genomic sequences (Monaco and Lehrach, *Proc. Natl. Acad. Sci. U.S.A.* 88:4123-7, 1991) is screened for the DLC-1 gene by the polymerase chain reaction (PCR). The library is arranged in a number (e.g., 39) of primary DNA pools, prepared from high-density grids each containing around 300-400 YAC clones. Primary pools are screened by PCR to identify a pool which contains a positive clone. A secondary PCR screen is then performed on the appropriate set of eight row and 12 column pools, as described by Bentley et al. (*Genomics* 12:534-41, 1992). PCR primers based on the DLC-1 cDNA sequence are used as a sequence tagged site (STS) for the 3' region of the gene. The yeast DNA is then amplified with these primers by PCR for 30 cycles of 94° C. for 1 minute, 60° C. for 1 minute and 72° C. for 1 minute, with a final 5 minute extension at 72° C. Confirmation that positive YAC clones contain the majority of the coding sequence of the DLC-1 genomic gene is obtained by amplification of an STS from the 5' end of the cDNA. Exon boundaries of the DLC-1 gene are then characterized, e.g., by the vectorette PCR method. This strategy has been described in detail previously (Roberts et al., *Genomics* 13:942-50, 1992).

With the sequences of the DLC-1 cDNA and DLC-1 gene in hand, primers derived from these sequences may be used in diagnostic tests (described below) to determine the presence of mutations in any part of the genomic DLC-1 gene of a patient. Such primers will be oligonucleotides comprising a fragment of sequence from the DLC-1 gene (either intron sequence, exon sequence or a sequence spanning an intron-exon boundary) and will comprise at least 15 consecutive nucleotides of the DLC-1 cDNA or gene. It will be appreciated that greater specificity may be achieved by using primers of greater lenghts. Thus, in order to obtain enhanced specificity, the primers used may comprise 20, 25, 30 or even 50 consecutive nucleotides of the DLC-1 cDNA or gene. Furthermore, with the provision of the DLC-1 intron sequence information the analysis of a large and as yet untapped source of patient material for mutations will now be possible using methods such as chemical cleavage of mismatches (Cotton et al., *Proc Natl. Acad. Sci USA.* 85:4397-401, 1988; Montandon et al., *Nucleic Acids Res.* 9:3347-58, 1989) and single-strand conformational polymorphism analysis (Orita et al., *Genomics* 5:874-879, 1989).

Additional experiments may now be performed to identify and characterize regulatory elements flanking the DLC-1 gene. These regulatory elements may be characterized by standard techniques including deletion analyses wherein successive nucleotides of a putative regulatory region are removed and the effect of the deletions are studied by either transient or long-term expression analyses experiments. The identification and characterization of regulatory elements flanking the genomic DLC-1 gene may be made by functional experimentation (deletion analyses, etc.) in mammalian cells by either transient or long-term expression analyses.

Having provided a genomic clone for the human DLC-1 gene (Seq. I.D. Nos. 14-19), it will be apparent to one skilled in the art that either the genomic clone or the cDNA or sequences derived from these clones may be utilized in applications of this invention, including but not limited to, studies of the expression of the DLC-1 gene, studies of the function of the DLC-1 protein, the generation of antibodies to the DLC-1 protein diagnosis and therapy of DLC-1 deleted or mutated patients to prevent or treat the onset of HCC. Descriptions of applications describing the use of DLC-1 cDNA are therefore intended to comprehend the use of the genomic DLC-1 gene. It will also be apparent to one skilled in the art that homologs of this gene may now be cloned from other species, such as the rat or the mouse, by standard cloning methods. Such homologs will be useful in the production of animal models of HCC.

To facilitate the detection of point mutations in liver and other cancers that exhibit alteration at region 8p12-22, the human DLC-1 gene was cloned and the intron/exon sequences characterized (Seq. I.D. Nos. 14-19 and FIG. 9).

Figure 9:
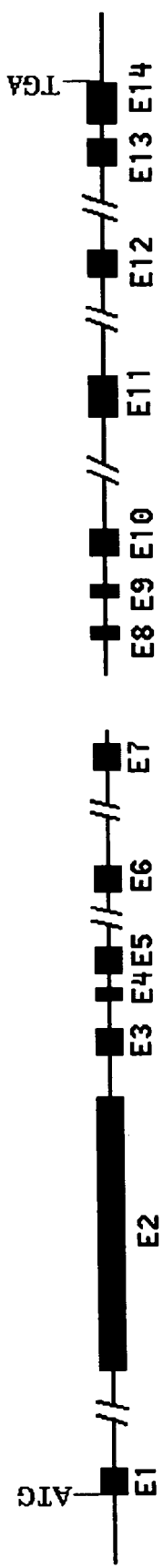
FIG. 9 is a schematic drawing of the human DLC-1 gene. Exons 1-14 are represented by boxes, with introns represented by the lines connecting the boxes.

Human DLC-1 is approximately 25 kb, and contains 14 exons. The largest exon is exon 2, at 1.5 kb, while the remaining exons are less than 300 bp on average (FIG. 9).

EXAMPLE 7

Cloning Mouse DLC-1

A full understanding of the function of DLC-1 and its role in cancer development is essential. This understanding can be facilitated by the generation of knock-out mice, which contain a non-functional DLC-1 gene. Prior to generating knock-out mice, the partial cDNA (Seq. I.D. Nos. 26-31) and partial genomic (Seq. I.D. Nos. 20-25) mouse DLC-1 sequences were determined.

Mouse DLC-1 genomic DNA was cloned and localized to chromosome 8 by FISH (see above for methods) using a mouse DLC-1 genomic DNA clone as the probe. Mouse DLC-1 is in a syntenic region of the human DLC-1 gene. The localization of DLC-1 gene in mice may permit studies with in vivo models for carcinogenesis.

EXAMPLE 8

Generating Transgenic Mice

Methods for generating transgenic mice are described in *Gene Targeting*, A. L. Joyuner ed., Oxford University Press, 1995 and Watson, J. D. et al., *Recombinant DNA* $2^{nd}$ Ed., W. H. Freeman and Co., New York, 1992, Chapter 14. To specifically generate transgenic mice containing a functional deletion of the DLC-1 gene, a 1.5 kb fragment in the front of exon 2 and another 5.5 kb fragment spanning from intron 2 to intron 5 were used as short arm and long arm, respectively. Between long arm and short arm, the neo gene was introduced, generating the vector shown in FIG. 10, referred to as the knock-out vector herein.

Figure 10:
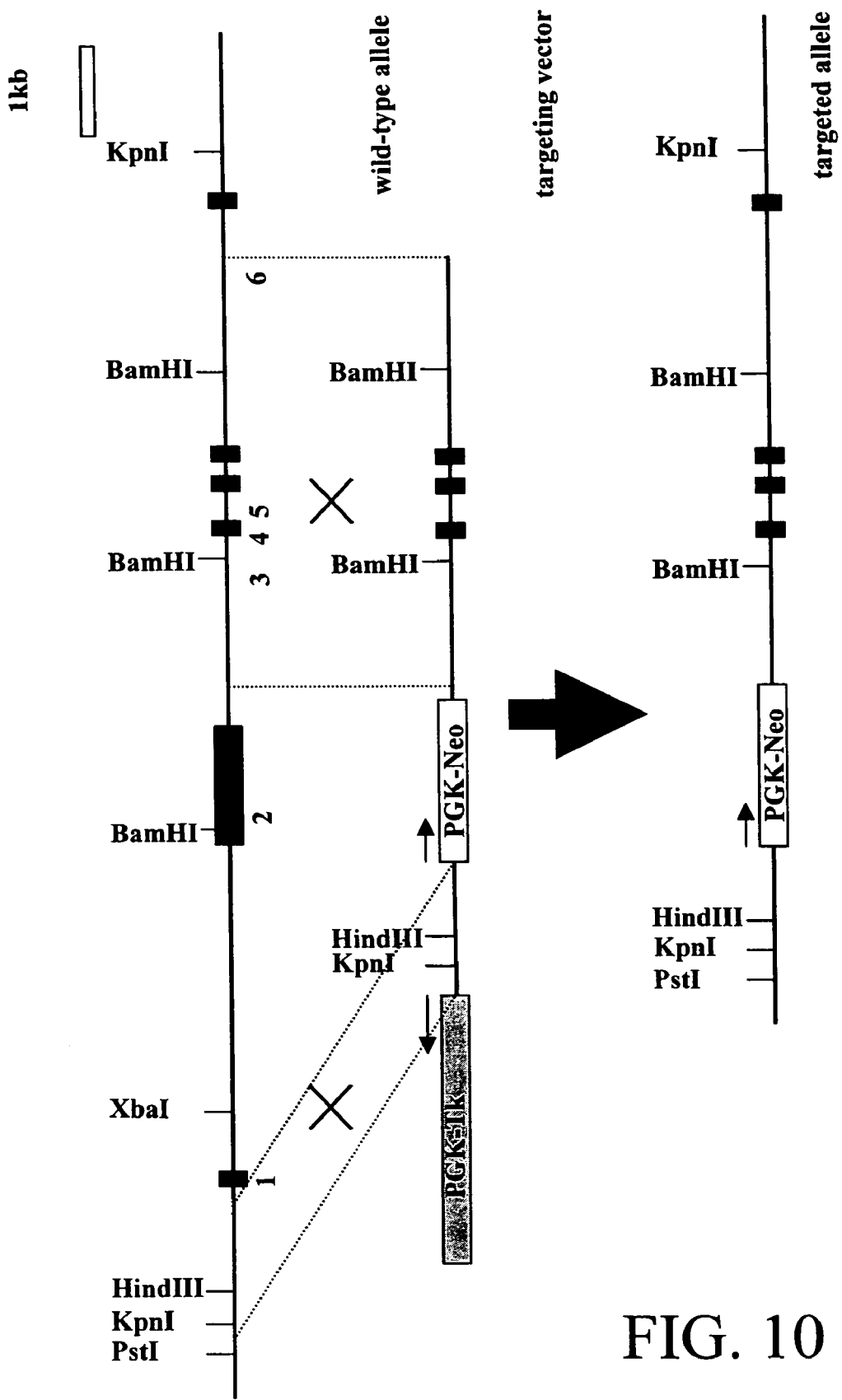
FIG. 10 is a schematic drawing of how the mouse DLC-1 gene was targeted using homologous recombination. The resulting construct can be used to generate DLC-1 homozygous knock-out mice.

Using standard transgenic mouse technology, the vector shown in FIG. 10 can be used to generate DLC-1 knock-out mice by homologous recombination. The knock-out vector is introduced into embryonic stem cells (ES cells) by standard methods which may include transfection, retroviral infection or electroporation (also see Example 11). The transfected ES cells expressing the knock-out vector will grow in medium containing the antibiotic G418. The neomycin resistant ES cells will be microinjected into mouse embryos (blastocysts), which are implanted into the uterus of pseudopregnant mice. The litter will be screened for chimeric mice by observing their coat color. Chimeric mice are ones in which the injected ES cells developed into the germ line, thereby allowing transmission of the gene to their offspring. The resulting heterozygotic mice will be mated to generate a homozygous line of transgenic mice functionally deleted for DLC-1. These homozygous mice will then be screened phenotypically, for example, their predisposition to developing cancer.

EXAMPLE 9

Preferred Method of Making the DLC-1 cDNA

The foregoing discussion describes the original means by which the DLC-1 cDNA was obtained and also provides the nucleotide sequence of this clone. With the provision of this sequence information, the polymerase chain reaction (PCR) may now be utilized in a more direct and simple method for producing the DLC-1 cDNA.

Essentially, total RNA is extracted from human cells by any one of a variety of methods routinely used; Sambrook et al. (*Molecular Cloning: A Laboratory Manual*, Cold Spring Harbor, N.Y., 1989) and Ausubel et al. (In *Current Protocols in Molecular Biology*, Greene Publishing Associates and Wiley-Intersciences, 1987) provide descriptions of methods for RNA isolation. Any human cell line derived from a non-DLC-1 deleted individual would be suitable, such as the widely used HeLa cell line, or the WI-38 human skin fibroblast cell line available from the American Type Culture Collection, Rockville, Md. The extracted RNA is then used as a template for performing the reverse transcription-polymerase chain reaction (RT-PCR) amplification of cDNA. Methods and conditions for RT-PCR are described in Kawasaki et al. (In *PCR Protocols, A Guide to Methods and Applications*, Innis et al. (eds.), pp. 21-27, Academic Press, Inc., San Diego, Calif., 1990). The selection of PCR primers will be made according to the portions of the cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (*PCR Protocols, A Guide to Methods and Applications*, Innis et al. (eds.), Academic Press, Inc., San Diego, Calif., 1990). The entire DLC-1 cDNA molecule may be amplified using the following combination of primers:

5' TAT GGG CTC GAG CGG CCG CCC 3' (Seq. I.D. No. 3)

5' CGC ACA GTC TTA CAT ATT CCA 3' (Seq. I.D. No. 4)

The open reading frame of the cDNA molecule may be amplified using the following combination of primers:

5' ATG TGC AGA AAG AAG CCG GAC ACC 3' (Seq. I.D. No. 5)

5' CCT AGA TTT GGT GTC TTT GGT TTC 3' (Seq. I.D. No. 6)

These primers are illustrative only; it will be appreciated by one skilled in the art that many different primers may be derived from the provided cDNA sequence in order to amplify particular regions of these cDNAs.

EXAMPLE 10

Sequence Variants of DLC-1

The nucleotide sequence of the DLC-1 cDNA is set forth is SEQ ID NO: 1 and the amino acid sequence of the DLC-1 protein encoded by that cDNA is set forth in SEQ ID NO: 2. Having presented the nucleotide sequence of the DLC-1 cDNA and the amino acid sequence of the protein, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (In *Molecular Cloning: A Laboratory Manual*, Cold Spring Harbor, N.Y., 1989, Ch. 15). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the DLC-1 protein are comprehended by this invention. Also within the scope of this invention are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of the DLC-1 cDNA molecule or the DLC-1 gene and, for the purposes of PCR, will comprise at least a 15 nucleotide sequence and, more preferably, a 20-50 nucleotide sequence of the DLC-1 cDNA (Seq. I.D. No. 1) or the DLC-1 gene (Seq. I.D. Nos. 14-19) (i.e., at least 20-50 consecutive nucleotides of the DLC-1 cDNA or gene sequences). DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In *Molecular Cloning: A Laboratory Manual*, Cold Spring Harbor, N.Y., 1989 ch. 9 and 11), herein incorporated by reference. By way of illustration only, a hybridization experiment may be performed by hybridization of a DNA molecule (for example, a deviation of the DLC-1 cDNA) to a target DNA molecule (for example, the DLC-1 cDNA) which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989). Hybridization with a target probe labeled with [$^{32}$P]-dCTP is generally carried out in a solution of high ionic strength such as 6×SSC at a temperature that is 20-25° C. below the melting temperature, $T_m$, described below. For such Southern hybridization experiments where the target DNA molecule on the Southern blot contains 10 ng of DNA or more, hybridization is typically carried out for 6-8 hours using 1-2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, *Proc. Natl. Acad. Sci. USA* 48:1390, 1962):

$$T_m = 81.5° C. - 16.6(\log_{10}[Na^+]) + 0.41(\% \, G+C) - 0.63(\% \, \text{formamide}) - (600/l)$$

Where l=the length of the hybrid in base pairs.

This equation is valid for concentrations of $Na^+$ in the range of 0.01 M to 0.4 M, and it is less accurate for calculations of $T_m$ in solutions of higher [$Na^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from the open reading frame of the DLC-1 cDNA (with a hypothetical % GC=45%), a calculation of hybridization conditions required to give particular stringencies may be made as follows:

For this example, it is assumed that the filter will be washed in 0.3×SSC solution following hybridization, thereby:

[Na$^+$]=0.045M
% GC=45%
Formamide concentration=0
l=150 base pairs $$T_m = 81.5 - 16(\log_{10}[\text{Na}^+]) + (0.41 \times 45) - \frac{(600)}{(150)}$$

and so $T_m$=74.4° C.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target DLC-1 cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target DLC-1 cDNA molecule will not hybridize. The above example is given entirely by way of theoretical illustration. One skilled in the art will appreciate that other hybridization techniques may be utilized and that variations in experimental conditions will necessitate alternative calculations for stringency.

In particular embodiments of the present invention, stringent conditions may be defined as those under which DNA molecules with more than 25% sequence variation (also termed "mismatch") will not hybridize. In a more particular embodiment, stringent conditions are those under which DNA molecules with more than 15% mismatch will not hybridize, and more preferably still, stringent conditions are those under which DNA sequences with more than 10% mismatch will not hybridize. In another embodiment, stringent conditions are those under which DNA sequences with more than 6% mismatch will not hybridize.

The degeneracy of the genetic code further widens the scope of the present invention as it enables major variations in the nucleotide sequence of a DNA molecule while maintaining the amino acid sequence of the encoded protein. For example, the sixteenth amino acid residue of the DLC-1 protein is alanine. This is encoded in the DLC-1 cDNA by the nucleotide codon triplet GCC. Because of the degeneracy of the genetic code, three other nucleotide codon triplets, GCT, GCG and GCA, also code for alanine. Thus, the nucleotide sequence of the DLC-1 cDNA could be changed at this position to any of these three codons without affecting the amino acid composition of the encoded protein or the characteristics of the protein. The genetic code and variations in nucleotide codons for particular amino acids is presented in Tables 1 and 2. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

The invention also includes DNA sequences that are substantially identical to any of the DNA sequences disclosed herein, where substantially identical means a sequence that has identical nucleotides in at least 75% of the aligned nucleotides, for example 80%, 85%, 90%, 95% or 98% identity of the aligned sequences.

TABLE 1

The Genetic Code

| First Position | Second Position | | | | (3' end) | Third |
|---|---|---|---|---|---|---|
| (5' end) | T | C | A | | G | Position |
| T | Phe | Ser | Tyr | | Cys | T |
| | Phe | Ser | Tyr | | Cys | C |
| | Leu | Ser | Stop (och) | | Stop | A |
| | Leu | Ser | Stop (amb) | | Trp | G |
| C | Leu | Pro | His | | Arg | T |
| | Leu | Pro | His | | Arg | C |
| | Leu | Pro | Gln | | Arg | A |
| | Leu | Pro | Gln | | Arg | G |
| A | Ile | Thr | Asn | | Ser | T |
| | Ile | Thr | Asn | | Ser | C |
| | Ile | Thr | Lys | | Arg | A |
| | Met | Thr | Lys | | Arg | G |
| G | Val | Ala | Asp | | Gly | T |
| | Val | Ala | Asp | | Gly | C |
| | Val | Ala | Glu | | Gly | A |
| | Val (Met) | Ala | Glu | | Gly | G |

"Stop (och)" stands for the ochre termination triplet, and
"Stop" (amb)" for the amber.
ATG is the most common initiator codon;
GTG usually codes for valine, but it can also code for methionine to initiate an mRNA chain.

TABLE 2

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the DNA mutagenesis techniques described above may be used not only to produce variant DNA molecules, but will also facilitate the production of proteins which differ in certain structural aspects from the DLC-1 protein, yet which proteins are clearly derivative of this protein and which maintain the essential characteristics of the DLC-1 protein. Newly derived proteins may also be selected in order to obtain variations on the characteristic of the DLC-1 protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 3 when it is desired to finely modulate the characteristics of the protein. Table 3 shows amino acids which may be substituted for an original amino acid in a protein and which are regarded as conservative substitutions.

TABLE 3

| Original Residue | Conservative Substitutions |
|---|---|
| Ala | Ser |
| Arg | Lys |
| Asn | gln, his |
| Asp | Glu |
| Cys | Ser |
| Gln | Asn |
| Glu | Asp |
| Gly | Pro |
| His | asn; gln |
| Ile | leu, val |
| Leu | ile; val |
| Lys | arg; gln; glu |
| Met | leu; ile |
| Phe | met; leu; tyr |
| Ser | Thr |
| Thr | Ser |
| Trp | Tyr |
| Tyr | trp; phe |
| Val | ile; leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the DLC-1 protein by assays in which DNA molecules encoding the derivative proteins are transfected into DLC-1 cells using routine procedures.

The DLC-1 gene, DLC-1 cDNA, DNA molecules derived therefrom and the protein encoded by the cDNA and derivatives thereof may be utilized in aspects of both the study of HCC and for diagnostic and therapeutic applications related to HCC. Utilities of the present invention include, but are not limited to, those utilities described in the examples presented herein. Those skilled in the art will recognize that the utilities herein described are not limited to the specific experimental modes and materials presented and will appreciate the wider potential utility of this invention.

EXAMPLE 11

Expression of DLC-1 cDNA Sequences

With the provision of the DLC-1 cDNA (Seq. I.D. No. 1), the expression and purification of the DLC-1 protein by standard laboratory techniques is now enabled. The purified protein may be used for functional analyses, antibody production, diagnostics and patient therapy. Furthermore, the DNA sequence of the DLC-1 cDNA can be manipulated in studies to understand the expression of the gene and the function of its product. Mutant forms of the DLC-1 may be isolated based upon information contained herein, and may be studied in order to detect alteration in expression patterns in terms of relative quantities, tissue specificity and functional properties of the encoded mutant DLC-1 protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to DLC-1 proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Cold Spring Harbor, N.Y., 1989, ch. 17) herein incorporated by reference. Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (*Molecular Cloning: A Laboratory Manual*, Cold Spring Harbor, N.Y., 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Cold Spring Harbor, N.Y., 1989, ch. 17). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al.,

*Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). DLC-1 fusion proteins may be isolated from protein gels, lyophilized, ground into a powder and used as an antigen. The DNA sequence can also be transferred from its existing context in pREP4 to other cloning vehicles, such as other plasmids, bacteriophages, cosmids, animal viruses and yeast artificial chromosomes (YACs) (Burke et al., *Science* 236:806-12, 1987). These vectors may then be introduced into a variety of hosts including somatic cells, and simple or complex organisms, such as bacteria, fungi (Timberlake and Marshall, *Science* 244:1313-7, 1989), invertebrates, plants (Gasser and Fraley, *Science* 244:1293, 1989), and pigs (Pursel et al., *Science* 244:1281-8, 1989), which cell or organisms are rendered transgenic by the introduction of the heterologous DLC-1 cDNA.

For expression in mammalian cells, the cDNA sequence may be ligated to heterologous promoters, such as the simian virus (SV) 40, promoter in the pSV2 vector (Mulligan and Berg, *Proc. Nail. Acad. Sci. USA* 78:2072-6, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-41, 1982) and mycophenolic acid (Mulligan and Berg, *Proc. Natl. Acad. Sci. USA* 78:2072-6, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan and Berg, *Proc. Natl. Acad. Sci. USA* 78:2072-6, 1981; Gorman et al., *Proc. Nail. Acad Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In: *Genetically Altered Viruses and the Environment*, Fields et al. (Eds.) 22:319-328, Cold Spring Harbor Laboratory Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-6, 1981) or neo (Southern and Berg, *J. Mol. Appl. Genet.* 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-7, 1980), or pellet guns (Klein et al., *Nature* 327:70, 1987). Alternatively, the cDNA can be introduced by infection with virus vectors. Systems are developed that use, for example, retroviruses (Bernstein et al., Gen. Engrg. 7:235, 1985), adenoviruses (Ahmad et al., *J. Virol.* 57:267, 1986), or Herpes virus (Spaete et al, *Cell* 30:295, 1982).

These eukaryotic expression systems can be used for studies of the DLC-1 gene and mutant forms of this gene, the DLC-1 protein and mutant forms of this protein. Such uses include, for example, the identification of regulatory elements located in the 5' region of the DLC-1 gene on genomic clones that can be isolated from human genomic DNA libraries using the information contained in the present invention. The eukaryotic expression systems may also be used to study the function of the normal complete protein, specific portions of the protein, or of naturally occurring or artificially produced mutant proteins.

Using the above techniques, the expression vectors containing the DLC-1 gene sequence or fragments or variants or mutants thereof can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts (as described herein) may be used.

The following is provided as one exemplary method to express DLC-1 polypeptide from the cloned DLC-1 cDNA sequences in mammalian cells. Cloning vector pXTI, commercially available from Stratagene, contains the Long Terminal Repeats (LTRs) and a portion of the GAG gene from Moloney Murine Leukemia Virus. The position of the viral LTRs allows highly efficient, stable transfection of the region within the LTRs. The vector also contains the Herpes Simplex Thymidine Kinase promoter (TK), active in embryonal cells and in a wide variety of tissues in mice, and a selectable neomycin gene conferring G418 resistance. Two unique restriction sites BglII and XhoI are directly downstream from the TK promoter. DLC-1 cDNA, including the entire open reading frame for the DLC-1 protein and the 3' untranslated region of the cDNA is cloned into one of the two unique restriction sites downstream from the promoter.

The ligated product is transfected into mouse NIH 3T3 cells using Lipofectin (Life Technologies, Inc.) under conditions outlined in the product specification. Positive transfectants are selected after growing the transfected cells in 600 µg/ml G418 (Sigma, St. Louis, Mo.). The protein is released into the supernatant and may be purified by standard immunoaffinity chromatography techniques using antibodies raised against the DLC-1 protein, as described below.

Expression of the DLC-1 protein in eukaryotic cells may also be used as a source of proteins to raise antibodies. The DLC-1 protein may be extracted following release of the protein into the supernatant as described above, or, the cDNA sequence may be incorporated into a eukaryotic expression vector and expressed as a chimeric protein with, for example, β-globin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene). This vector encodes rabbit β-globin.

The present invention thus encompasses recombinant vectors which comprise all or part of the DLC-1 gene or cDNA sequences, for expression in a suitable host. The DLC-1 DNA is operatively linked in the vector to an expression control sequence in the recombinant DNA molecule so that the DLC-1 polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant DLC-1 DNA sequences, similar systems are employed to express and produce the mutant product.

EXAMPLE 12

Production of an Antibody to DLC-1 Protein

Monoclonal or polyclonal antibodies may be produced to either the normal DLC-1 protein or mutant forms of this protein. Optimally, antibodies raised against the DLC-1 protein would specifically detect the DLC-1 protein. That is, such antibodies would recognize and bind the DLC-1 protein and would not substantially recognize or bind to other proteins found in human cells. The determination that an antibody specifically detects the DLC-1 protein is made by any one of a number of standard immunoassay methods; for instance, the Western blotting technique (Sambrook et al., *Molecular Cloning: A Laboratory Manual*, Cold Spring Harbor, N.Y., 1989). To determine that a given antibody preparation (such as one produced in a mouse) specifically detects the DLC-1 protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the DLC-1 protein will, by this technique, be shown to bind to the DLC-1 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-DLC-1 protein binding.

Substantially pure DLC-1 protein suitable for use as an immunogen is isolated from transfected or transformed cells. Concentration of protein in the final preparation is adjusted, for example, by concentration on an Amicon filter device, to the level of a few micrograms per milliliter. Monoclonal or polyclonal antibody to the protein can then be prepared as follows:

Monoclonal Antibody Production by Hybridoma Fusion

Monoclonal antibody to epitopes of the DLC-1 protein identified and isolated as described can be prepared from murine hybridomas according to the classical method of Kohler and Milstein (Nature 256:495, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, Cold Spring Harbor Laboratory, New York, 1988).

Polyclonal Antibody Production by Immunization

Polyclonal antiserum containing antibodies to heterogenous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (*J. Clin. Endocrinol. Metab.* 33:988-91, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19, Blackwell, 1973). Plateau concentration of antibody is usually in the range of 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

Antibodies Raised against Synthetic Peptides

A third approach to raising antibodies against the DLC-1 protein is to use synthetic peptides synthesized on a commercially available peptide synthesizer based upon the predicted amino acid sequence of the DLC-1 protein.

Antibodies Raised by Injection of DLC-1 Gene

Antibodies may be raised against the DLC-1 protein by subcutaneous injection of a DNA vector which expresses the DLC-1 protein into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:1524, 1992). Expression vectors suitable for this purpose may include those which express the DLC-1 gene under the transcriptional control of either the human mactin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

EXAMPLE 13

DNA-Based Diagnosis

One major application of the DLC-1 sequence information presented herein is in the area of genetic testing for predisposition to HCC, BC, PC and/or CRC owing to DLC-1 deletion or mutation. The gene sequence of the DLC-1 gene, including intron-exon boundaries is also useful in such diagnostic methods. Individuals carrying mutations in the DLC-1 gene, or having heterozygous or homozygous deletions of the DLC-1 gene, may be detected at the DNA level with the use of a variety of techniques. For such a diagnostic procedure, a biological sample of the subject, which biological sample contains either DNA or RNA derived from the subject, is assayed for a mutated or deleted DLC-1 gene. Suitable biological samples include samples containing genomic DNA or RNA obtained from body cells, such as those present in peripheral blood, urine, saliva, tissue biopsy, surgical specimen, amniocentesis samples and autopsy material. The detection in the biological sample of either a mutant DLC-1 gene, a mutant DLC-1 RNA, or a homozygously or heterozygously deleted DLC-1 gene, may be performed by a number of methodologies, as outlined below.

A preferred embodiment of such detection techniques is the polymerase chain reaction amplification of reverse transcribed RNA (RT-PCR) of RNA isolated from lymphocytes followed by direct DNA sequence determination of the products. The presence of one or more nucleotide differences between the obtained sequence and the cDNA sequences, and especially, differences in the ORF portion of the nucleotide sequence are taken as indicative of a potential DLC-1 gene mutation.

Alternatively, DNA extracted from lymphocytes or other cells may be used directly for amplification. The direct amplification from genomic DNA would be appropriate for analysis of the entire DLC-1 gene including regulatory sequences located upstream and downstream from the open reading frame. Recent reviews of direct DNA diagnosis have been presented by Caskey (*Science* 236:1223-8, 1989) and by Landegren et al. (*Science* 242:229-37, 1989).

Further studies of DLC-1 genes isolated from DLC-1 patients may reveal particular mutations, or deletions, which occur at a high frequency within this population of individuals. In this case, rather than sequencing the entire DLC-1 gene, it may be possible to design DNA diagnostic methods to specifically detect the most common DLC-1 mutations or deletions.

The detection of specific DNA mutations may be achieved by methods such as hybridization using specific oligonucleotides (Wallace et al., *Cold Spring Harbor Symp. Quant. Biol.* 51:257-61, 1986), direct DNA sequencing (Church and Gilbert, *Proc. Natl. Acad Sci USA* 81:1991-5, 1988), the use of restriction enzymes (Flavell et al., *Cell* 15:25, 1978; Geever et al., *Proc. Natl. Acad Sci USA* 78:5081, 1981), discrimination on the basis of electrophoretic mobility in gels with denaturing reagent (Myers and Maniatis, *Cold Spring Harbor Symp. Quant. Biol.* 51:275-84, 1986), RNase protection (Myers et al., *Science* 230:1242, 1985), chemical cleavage (Cotton et al., *Proc. Natl. Acad. Sci. USA* 85:4397-401, 1988), and the ligase-mediated detection procedure (Landegren et al., *Science* 241:1077, 1988).

Oligonucleotides specific to normal or mutant sequences are chemically synthesized using commercially available machines, labeled radioactively with isotopes (such as $^{32}P$) or non-radioactively, with tags such as biotin (Ward and Langer et al., *Proc. Natl. Acad. Sci. USA* 78:6633-57, 1981), and hybridized to individual DNA samples immobilized on membranes or other solid supports by dot-blot or transfer from gels after electrophoresis. The presence of these specific sequences are visualized by methods such as autoradiography or fluorometric (Landegren, et al., *Science* 242:229-37, 1989) or colorimetric reactions (Gebeyehu et al., *Nucleic Acids Res.* 15:4513-34, 1987). The absence of hybridization would indicate a mutation in the particular region of the gene, or deleted DLC-1 gene.

Sequence differences between normal and mutant forms of the DLC-1 gene may also be revealed by the direct DNA sequencing method of Church and Gilbert (*Proc. Nail Acad. Sci. USA* 81:1991-5, 1988). Cloned DNA segments may be used as probes to detect specific DNA segments. The sensitivity of this method is greatly enhanced when combined with PCR (Wrichnik et al., *Nucleic Acids Res.* 15:52942, 1987; Wong et al., *Nature* 330:384-386, 1987; Stoflet et al., *Science* 239:491-4, 1988). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, *J. Mol. Biol.* 98:503, 1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734; Nagamine et al., *Am. J. Hum. Genet.* 45:337-9, 1989). DNA fragments of different sequence compositions may be distinguished on denaturing formamide gradient gels in which the mobilities of different DNA fragments are retarded in the gel at different positions according to their specific "partial-melting" temperatures (Myers et al., *Science* 230:1242, 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., *Proc. Nat. Acad. Sci. USA* 86:6230-4, 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the DLC-1 gene, a system capable of detecting such multiple mutations would be desirable. For example, a PCR with multiple, specific oligonucleotide primers and hybridization probes may be used to identify all possible mutations at the same time (Chamberlain et al., *Nucl. Acids Res.* 16:1141-55, 1988). The procedure may involve immobilized sequence-specific oligonucleotides probes (Saiki et al., *Proc. Nat Acad. Sci. USA* 86:6230-4, 1989).

The following Example describes one method by which deletions of the DLC-1 gene may be detected.

EXAMPLE 14

Two Step Assay to Detect the Presence of DLC-1 Gene in a Sample

Patient liver, breast, prostate and/or colorectal tissue sample is processed according to the method disclosed by Antonarakis, et al. (*New Eng. J. Med.* 313:842-848, 1985), separated through a 1% agarose gel and transferred to a nylon membrane for Southern blot analysis. Membranes are UV cross linked at 150 mJ using a GS Gene Linker (Bio-Rad). A DLC-1 probe is subcloned into pTZ18U. The phagemids are transformed into *E. coli* MV 1190 infected with M13KO7 helper phage (Bio-Rad, Richmond, Calif.). Single stranded DNA is isolated according to standard procedures (see Sambrook, et al. *Molecular Cloning: A Laboratory Manual*, Cold Spring Harbor, N.Y., 1989).

Blots are prehybridized for 15-30 min. at 65° C. in 7% sodium dodecyl sulfate (SDS) in 0.5M $NaPO_4$. The methods follow those described by Nguyen, et al. (*BioTechniques* 13:116-123, 1992). The blots are hybridized overnight at 65° C. in 7% SDS, 0.5M NaPO, with 25-50 ng/ml single stranded probe DNA. Post-hybridization washes consist of two 30 min. washes in 5% SDS, 40 mM $NaPO_4$ at 65° C., followed by two 30-min washes in 1% SDS, 40 mM $NaPO_4$ at 65° C.

Next the blots are rinsed with phosphate buffered saline (pH 6.8) for 5 min at room temperature and incubated with 0.2% casein in PBS for 5 min. The blots are then preincubated for 5-10 minutes in a shaking water bath at 45° C. with hybridization buffer consisting of 6M urea, 0.3M NaCl, and 5× Denhardt's solution (see Sambrook, et al., *Molecular Cloning: A Laboratory Manual*, Cold Spring Harbor, N.Y., 1989). The buffer is removed and replaced with 50-75 $\mu$l/cm$^2$ fresh hybridization buffer plus 2.5 nM of the covalently cross-linked oligonucleotide sequence complementary to the universal primer site (UP-AP, Bio-Rad). The blots are hybridized for 20-30 min at 45° C. and post hybridization washes are incubated at 45° C. as two 10 min washes in 6 M urea, 1× standard saline citrate (SSC), 0.1% SDS and one 10 min wash in 1×SSC, 0.1% Triton® X-100. The blots are rinsed for 10 min at room temperature with 1×SSC.

Blots are incubated for 10 min at room temperature with shaking in the substrate buffer consisting of 0.1 M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of the DLC-1 gene. Patient samples which show no hybridizing bands lack the DLC-1 gene, indicating the possibility of ongoing cancer, or an enhanced susceptibility to developing cancer in the future.

EXAMPLE 15

Quantitation of DLC-1 Protein

An alternative method of diagnosing DLC-1 gene deletion or mutation is to quantitate the level of DLC-1 protein in the cells of an individual. This diagnostic tool would be useful for detecting reduced levels of the DLC-1 protein which result from, for example, mutations in the promoter regions of the DLC-1 gene or mutations within the coding region of the gene which produced truncated, non-functional polypeptides, as well as from deletions of the entire DLC-1 gene. The determination of reduced DLC-1 protein levels would be an alternative or supplemental approach to the direct determination of DLC-1 gene deletion or mutation status by the methods outlined above. The availability of antibodies specific to the DLC-1 protein will facilitate the quantitation of cellular DLC-1 protein by one of a number of immunoassay methods which are well known in the art and are presented in Harlow and Lane (*Antibodies, A Laboratory Manual*, Cold Spring Harbor Laboratory, New York, 1988).

For the purposes of quantitating the DLC-1 protein, a biological sample of the subject, which sample includes cellular proteins, is required. Such a biological sample may be obtained from body cells, such as those present in peripheral blood, urine, saliva, tissue biopsy, amniocentesis samples, surgical specimens and autopsy material, particularly liver cells. Quantitation of DLC-1 protein is achieved by immunoassay and compared to levels of the protein found in healthy cells. A significant (e.g., 50% or greater) reduction in the amount of DLC-1 protein in the cells of a subject compared to the amount of DLC-1 protein found in normal human cells would be taken as an indication that the subject may have deletions or mutations in the DLC-1 gene locus.

EXAMPLE 16

Gene Therapy

A new gene therapy approach for DLC-1 patients is now made possible by the present invention. Essentially, liver cells may be removed from a patient having deletions or mutations of the DLC-1 gene, and then transfected with an expression vector containing the DLC-1 cDNA. These transfected liver cells will thereby produce functional DLC-1 protein and can be reintroduced into the patient. In addition to liver cells, breast, colorectal, prostate, or other cells may be used, depending on the cancer of interest.

The scientific and medical procedures required for human cell transfection are now routine procedures. The provision herein of DLC-1 cDNAs now allows the development of human gene therapy based upon these procedures. Immunotherapy of melanoma patients using genetically engineered tumor-infiltrating lymphocytes (TILs) has been reported by Rosenberg et al. (*N. Engl. J. Med.* 323:570-8, 1990). In that study, a retrovirus vector was used to introduce a gene for neomycin resistance into TILs. A similar approach may be used to introduce the DLC-1 cDNA into patients affected by DLC-1 deletions or mutations.

Retroviruses have been considered the preferred vector for experiments in gene therapy, with a high efficiency of infection and stable integration and expression (Orkin et al., *Prog. Med Genet.* 7:130, 1988). The full length DLC-1 gene or cDNA can be cloned into a retroviral vector and driven from either its endogenous promoter or from the retroviral LTR (long terminal repeat). Other viral transfection systems may also be utilized for this type of approach, including Adeno-Associated virus (AAV) (McLaughlin et al., *J. Virol.* 62:1963, 1988), Vaccinia virus (Moss et al., *Annu. Rev. Immunol.* 5:305, 1987), Bovine Papilloma virus (Rasmussen et al., *Methods Enymol.* 139:642, 1987) or members of the herpesvirus group such as Epstein-Barr virus (Margolskee et al., *Mol. Cell. Biol.* 8:2837-47, 1988). Recent developments in gene therapy techniques include the use of RNA-DNA hybrid oligonucleotides, as described by Cole-Strauss, et al. (*Science* 273:1386-9, 1996). This technique may allow for site-specific integration of cloned sequences, permitting accurately targeted gene replacement.

Having illustrated and described the principles of isolating the human DLC-1 cDNA and its corresponding genomic genes, the protein and modes of use of these biological molecules, it should be apparent to one skilled in the art that the invention can be modified in arrangement and detail without departing from such principles. We claim all modifications coming within the spirit and scope of the claims presented herein.

We claim:

1. A method for diagnosing a cancer in a subject, comprising detecting a decreased level of a nucleic acid molecule comprising the nucleic acid sequence set forth as SEQ ID NO: 1 in a sample from the subject, compared to a non-cancerous control sample, wherein detection of the decreased level of the nucleic acid molecule in the sample from the subject, diagnoses the cancer.

2. The method of claim 1, wherein the cancer is breast cancer.

3. The method of claim 1, wherein the cancer is liver cancer.

4. The method of claim 1, wherein the cancer is colorectal cancer.

5. The method of claim 1, wherein the cancer is prostate cancer.

6. The method of claim 1, wherein the sample is a peripheral blood, a urine, a saliva, a tissue biopsy, surgical specimen, or an autopsy sample.

7. The method of claim 1, wherein the detection of the decreased level of the nucleic acid molecule in the sample from the subject comprises use of an amplification reaction, a hybridization reaction, or a change in electrophoretic mobility.

8. The method of claim 1, wherein the detection of the decreased level of the nucleic acid molecule in the sample from the subject comprises use of an amplification reaction, and the amplification reaction is polymerase chain reaction.

9. The method of claim 1, wherein the sample is a tissue biopsy, a surgical specimen, or an autopsy sample.

10. The method of claim 1, wherein the detection of the decreased level of the nucleic acid molecule in the sample from the subject comprises detecting decreased levels of the mRNA encoded by SEQ ID NO: 1 in a sample from the subject.

11. The method of claim 1, wherein the detection of the decreased level of the nucleic acid molecule in the sample from the subject comprises detecting a deletion of SEQ ID NO: 1 in a sample from the subject.

12. The method of claim 1 wherein the cancer is an adenocarcinoma.

13. The method of claim 12 wherein the adenocarcinoma is prostate cancer.

14. The method of claim 12 wherein the adenocarcinoma is colorectal cancer.

15. The method of claim 1 wherein the cancer is selected from liver cancer, breast cancer, colorectal cancer and prostate cancer.

16. A method for diagnosing liver cancer or breast cancer in a subject, comprising detecting a decreased level of a nucleic acid molecule comprising the nucleic acid sequence set forth as SEQ ID NO: 1 in a sample from the subject, compared to a non-cancerous control sample, wherein detection of the decreased level of the nucleic acid molecule in the sample from the subject diagnoses the cancer.

* * * * *